United States Patent [19]
Karger et al.

[11] Patent Number: 5,633,129
[45] Date of Patent: May 27, 1997

[54] ELECTROPHORETIC DETECTION AND SEPARATION OF MUTANT DNA USING REPLACEABLE POLYMER MATRICES

[75] Inventors: Barry L. Karger, Newton; William G. Thilly, Winchester; Frantisek Foret, Malden; Konstaintin Khrapko, Brookline, all of Mass.; Phouthone Koehavong, Pittsburgh, Pa.; Aharon S. Cohen, Newton; Roger W. Giese, Quincy, both of Mass.

[73] Assignees: Massachusetts Institute of Technology, Cambridge; Northeastern University, Boston, both of Mass.

[21] Appl. No.: 190,919

[22] Filed: Feb. 3, 1994

Related U.S. Application Data

[63] Continuation-in-part of Ser. No. 709,710, Jun. 3, 1991, abandoned, which is a continuation-in-part of Ser. No. 379,087, Jul. 13, 1989, Pat. No. 5,045,450.

[51] Int. Cl.$^6$ .................................................. C12Q 1/68
[52] U.S. Cl. ........................ 435/6; 435/18; 435/173.1; 435/283.1; 435/285.1; 435/287.1; 435/287.2; 435/289.1; 435/810; 422/68.1; 436/501; 536/22.1; 536/25.3; 536/25.4; 935/77; 935/78; 935/88
[58] Field of Search .......................... 435/6, 18, 173.1, 435/291, 310, 803, 808, 810, 820, 283.1, 285.1, 287.1, 287.2, 289.1; 436/501; 536/22.1, 25.3, 25.4; 935/77, 78, 88; 422/68.1

[56] References Cited

U.S. PATENT DOCUMENTS

| | | | |
|---|---|---|---|
| 4,683,195 | 7/1987 | Mullis et al. | 435/6 |
| 5,045,450 | 9/1991 | Thilly et al. | 435/6 |
| 5,087,559 | 2/1992 | Smith et al. | 435/6 |
| 5,112,460 | 5/1992 | Karger et al. | 204/182.8 |

FOREIGN PATENT DOCUMENTS

| | | |
|---|---|---|
| 2686621 | 7/1993 | France . |
| 89/02930 | 4/1989 | WIPO . |
| 90/13668 | 11/1990 | WIPO . |
| 91/00925 | 1/1991 | WIPO . |
| 93/19201 | 9/1993 | WIPO . |

OTHER PUBLICATIONS

Cohen et al. (1988) Proceedings of the National Acad. of Sci. (USA), vol. 85, pp. 9660–9663.
Heiger et al. (1990) J. of Chromatography, vol. 516, pp. 33–48.
Ganzler et al. (1992) Anal. Chem., vol. 64, pp. 2665–2671.
Myers et al. (1985) Nature, vol. 313, pp. 495–498.

(List continued on next page.)

*Primary Examiner*—Ardin H. Marschel
*Attorney, Agent, or Firm*—Hamilton, Brook, Smith & Reynolds, P.C.

[57] ABSTRACT

The disclosure relates to a method for resolving double-stranded DNA species differing by at least one base pair. Each of the species is characterized by an iso-melting domain with a unique melting temperature contiguous with a melting domain of higher thermal stability.

51 Claims, 11 Drawing Sheets

OTHER PUBLICATIONS

Cotton, R. G. H., "Current Methods of Mutation Detection," *Mutation Research*, 285:125–144 (1993).

Hovig, E. et al., "Constant Denaturant Gel Electrophoresis, a Modification of Denaturing Gradient Gel Electrophoresis, in Mutation Detection," *Mutation Research*, 262:63–71 (1991).

Castro A. et al., "Fluorescence Detection and Size Measurement of Single DNA Molecules," *Anal. Chem.*, 65:849–852 (1993).

Pariat, Y.F. et al., "Separation of DNA Fragments by Capillary Electrophoresis Using Replaceable Linear Polyacrylamide Matrices," *J. of Chromatography A.*, 652:57–66 (1993).

Ruiz–Martinez, M.C., et al., "DNA Sequencing by Capillary Electrophoresis with Replaceable Linear Polyacrylamide and Laser–Induced Fluorescence Detection," *Anal. Chem.*, 65:2851–2858 (1993).

Harris, C.C., "p. 53: At the Crossroads of Molecular Carcinogenesis and Risk Assessment," *Science*, 262:1980–1981 (1993).

Cariello, N.F., et al., "Resolution of a Missense Mutant in Human Genomic DNA by Denaturing Gradient Gel Electrophoresis and Direct Sequencing Using In Vitro DNA Amplification: $HPRT_{Munich}$," *Am. J. Hum. Genet.*, 42:726–734 (1988).

Karger, B.L., et al., "High–Performance Capillary Electrophoresis in the Biological Sciences," *J. of Chrom.*, 492:585–614 (1989).

Cohen, A.S. et al., "Separation and Analysis of DNA Sequence Reaction Products by Capillary Gel Electrophoresis," *J. of Chrom.* 516:49–60 (1990).

Kasper, T.J., et al., "Separation and Detection of DNA by Capillary Electrophoresis," *J. Chromatography*, 458:303–312 (1988).

Kuhr, W.G. and Yeung, E.S., "Optimization of Sensitivity and Separation in Capillary Zone Electrophoresis with Indirect Fluorescence Detection," *Anal. Chem.*, 60:2642–2646 (1988).

Fischer, S.G. and Lerman, L.S., "DNA Fragments Differing by Single Base–Pair Substitutions are Separated in Denaturing Gradient Gels: Corresponding with Melting Theory," *Proc. Natl. Acad. Sci. USA*, 80:1579–1583 (1983).

Wallingford, R.A. and Ewing A.G., "Capillary Zone Electrophoresis with Electrochemical Detection," *Anal. Chem.*, 59:1762–1766 (1987).

Gordon, M.J., et al., "Capillary Electrophoresis," *Science*, 242:224–228 (1988).

Smith, R.D., et al., "Improved Electrospray Ionization Interface for Capillary Zone Electrophoresis–Mass Spectrometry," *Anal. Chelm.*, 60:1948–1952.

Lee, E.D., et al., "On–Line Capillary Zone Electrophoresis–Ion Spray Tandem Mass Spectrometry for the Determination of Dynorphins," *J. Chromatography*, 458:313–321 (1988).

Porteous, D.J., "Rapid and Quantitative Detection of Unique Sequence Donor DNA in Extracts of Cultured Mammalian Cells: An Aid to Chromosome Mapping," *Som. Cell and Mol. Genet.*, 11(5):445–454 (1985).

Lerman, L.S., and Silverstein, K., "Computational Stimulation of DNA Melting and Its Application to Denaturing Gradient Gel Electrophoresis," *Methods in Enzymology*, 155:482–501 (1987).

Cohen, A.S., "Capillary Gel Electrophoresis of Biopolymers," *Friends in Analy. Chem.*, 12(5):195–202 (1993).

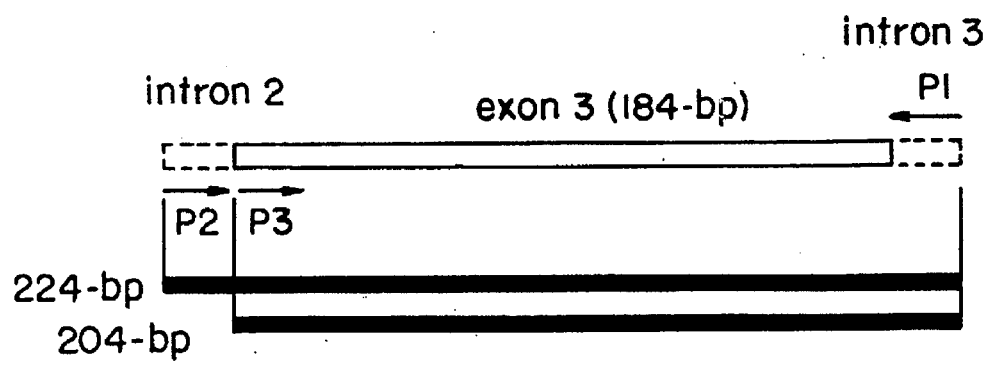
FIG. IA
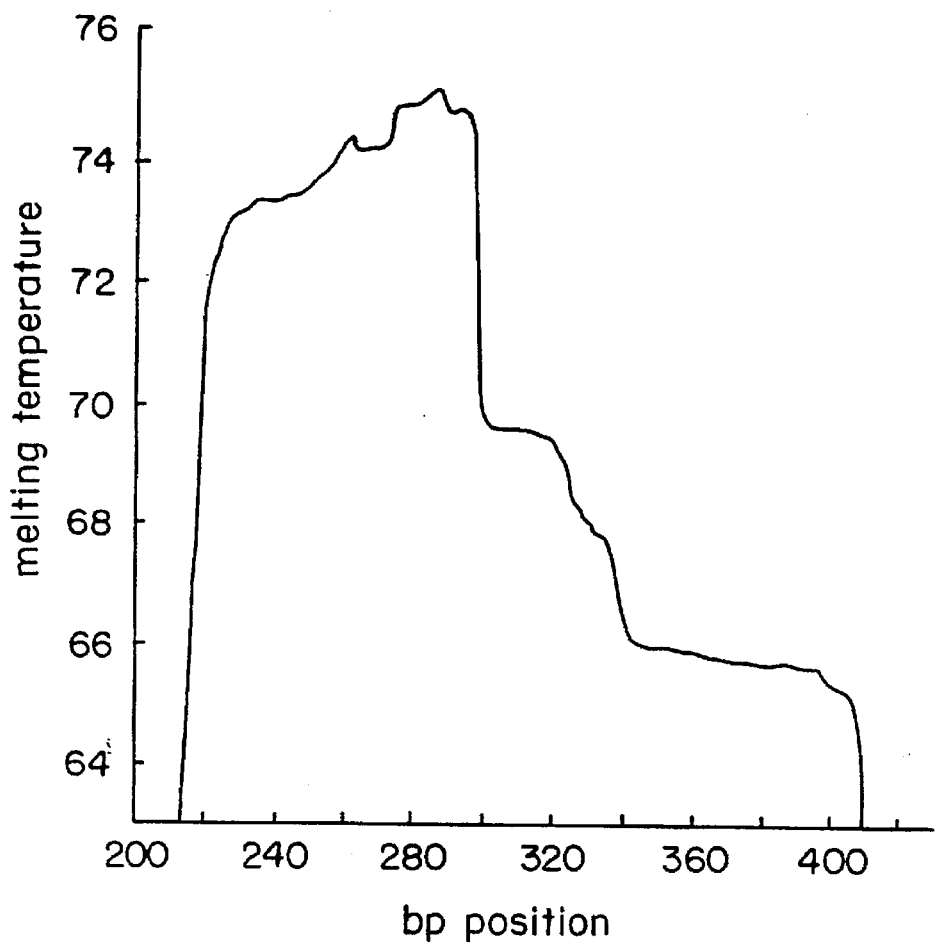
FIG. IB

ELECTROPHORETIC DETECTION AND SEPARATION OF MUTANT DNA USING REPLACEABLE POLYMER MATRICES

RELATED APPLICATION

This application is a continuation-in-part of U.S. Ser. No. 07/709,710, filed Jun. 3, 1992, now abandoned, which is a continuation-in-part of Ser. No. 07/379,087, filed Jul. 13, 1989, now issued U.S. Pat. No. 5,045,450, the teachings of which are herein incorporated by reference.

GOVERNMENT FUNDING

Work described herein was supported by grants from the U.S. National Institute for Environmental Health Sciences and the Department of Energy. The United States Government has certain rights in this invention.

BACKGROUND OF THE INVENTION

Variations in nucleic acid sequences and population polymorphisims are studied in the fields of biotechnology, mutagenesis, human genetics, and cancer genetics. A variation in nucleic acid sequence from what previously existed (wild type DNA) is called a mutation. Mutations can include changes in one, or several base pairs in the DNA sequence. Changes can include additions, deletions, inversions or substitutions.

In the field of genetic epidemiology, it is useful to be able to detect patterns of mutations to be probative of the causes of the mutations. In the field of pediatric genetics, detection of mutations is useful to screen for early diagnosis of rare genetic diseases in newborns. In genetic counseling of prospective parents, detection of mutations in their cells is anticipated to be of significant value. Detection of mutations is also useful in the production of biologically produced pharmaceuticals, such as vaccines or recombinant proteins to ascertain compliance with regulatory standards. The detection of mutations is also useful in toxicological studies to determine if genetic damage has occurred due to specific agents, such as additives in cosmetics or environmental contaminants.

Mutations at a specific gene locus (e.g., point mutations) may give rise to significantly altered cellular behavior. However, in any given sample of DNA which may contain mutant DNA, the fraction of mutated DNA molecules out of the total number of DNA molecules present varies greatly. Thus, many pathological conditions can manifest themselves even if only a small fraction of the DNA is mutated. For example, the ability to detect cancer cells by virtue of a mutation present in a small fraction of cells within a tissue or blood sample can be useful to detect metastasis of the cancer, to use as a signal that the cancer is recurring, or as a screen for the initial appearance of a cancer. Additionally, determining the mutational spectra of, for example, the tumor suppressor gene, p53, in non-tumorous tissue of a tumor bearing organ may lead to identification of the probable cause of an individual's tumor. (Harris, C. C., *Science*, 262:1980–1981 (Dec. 24, 1993).

A number of methods have been used to detect mutant DNA sequences, including isolation of DNA from cells, cloning and sequencing the cloned product. Several electrophoretic methods have been used to separate mutant DNA from wild type DNA including, for example, denaturing gradient gel electrophoresis (DGGE) (Fischer, S. G., and Lerman, L. S., *Proc. Natl. Acad. Sci. USA*, 80:1579–1583 (1983); Cariello, N. F., et al., *Am J. Hum. Genet.*, 42:726–734 (1988)). However, these methods are tedious and difficult to use. Further, certain common laboratory practices such as labeling DNA molecules with radioactive phosphorous created, in the course of several days, radiolysis reactions which interfere with these methods. Interfering reaction products are also found to arise due to thermolysis in separation extending for many hours at a temperature over 60° C., photochemical reactions with light from ordinary laboratory fluorescent fixtures, and from chemical reactions which presumably involve active oxygen species present in aqueous solutions.

Thus, a fast and reproducible method which can detect mutant DNA sequences present in a sample, including mutant DNA sequences that occur as a small fraction of DNA molecules relative to the total number of DNA molecules present in a sample, would be very important.

SUMMARY OF THE INVENTION

The present invention relates to a method of separating, or resolving, and detecting DNA molecules, including mutant DNA. The present invention also relates to a method of enriching in a sample containing mutant DNA, the fraction of mutant DNA relative to the total DNA in the sample. Specifically, the present invention relates to a method of resolving (i.e., physically separating) mutant nucleic acid sequences (e.g., DNA or RNA) from non-mutant (wild type) nucleic acid sequences. The method of the present invention uses partially denaturing conditions, a polymer matrix, and a high electrical field to provide a simple, rapid, and reproducible method for separating mutant DNA, or RNA, and wild type DNA, or RNA, sequences with high resolution. The present method also separates DNA, or RNA, which has been chemically reacted (e.g. methylated DNA) from unreacted DNA.

In the method of separation described herein, separation of mutant and non-mutant DNA molecules is based on the fact that the mobility (movement) of a partially melted (partially denatured) double-stranded DNA molecule in a high electric field within a polymer matrix is reduced as compared to an unmelted (fully annealed) double-stranded molecule. DNA or RNA sequences suitable for use in the present method contain two iso-melting domains: a first iso-melting domain, referred to as a low temperature iso-melting domain which melts at a first temperature, and a second iso-melting domain, referred to as a high temperature iso-melting domain, which melts at a second, higher temperature. The high temperature iso-melting domain is also referred to herein as a domain of higher thermal stability than the low temperature iso-melting domain. The two iso-melting domains are contiguous within the DNA or RNA sequence. (It is to be understood, that although the term DNA will be used from here on the description applies equally to RNA.) The term "melting" as defined herein, refers to the tendency of complementary duplex strands of DNA to separate from one another by forming two single strands of DNA. "Partially melted" as used herein, denotes the state of DNA of interest when the low-temperature iso-melting domain is melted but the high temperature iso-melting domain is fully annealed. An iso-melting domain is defined herein as a double-stranded DNA sequence in which all base pairs melt essentially simultaneously under certain conditions. Thus, depending upon the existing conditions, a particular DNA sequence is either fully annealed or fully melted. The presence of both a high temperature and a low temperature iso-melting domain within the DNA sequence ensures the existence, within a certain range of denaturant concentrations and/or temperature, of a stable, partially melted intermediate which contains both single-stranded and double-stranded DNA. An equilibrium exists between the fully melted and unmelted domain. Such an equilibrium is described in the field of statistical mechanics as a cooperative equilibrium.

When a mixture of double-stranded DNA molecules, containing a high and a low temperature iso-melting domain, differing by one or more base changes in the low temperature iso-melting domain, is electrophoresed on a polymer matrix under partially denaturing conditions (i.e., conditions which result in melting of the low temperature iso-melting domain but not the high temperature iso-melting domain), the duplexes display different states of cooperative equilibrium between the unmelted DNA and the partially melted species. The amount of time spent by the DNA molecules in the slower, partially melted form varies among specific sequences. Unmelted double-stranded DNA will migrate most rapidly through the polymer matrix, whereas the partially melted species will move more slowly. Therefore, the velocity of the partially melted form through the matrix is slower than the velocity of the unmelted form. As a result, nucleic acid molecules having base pair changes can be distinguished (separated) on the basis of their relative mobility through a polymer matrix.

An important step in the present method is the conversion of the mutant homoduplex DNA sequences obtained when isolating the DNA of interest into DNA heteroduplexes with the wild type DNA sequence. Typically, a DNA sample will contain a predominance of wild type sequence with a smaller fraction of mutant sequence present. By heating the sample containing wild type sequences and mutant sequences, the double-stranded sequences melt and form single-stranded sequences. These single-stranded sequences are then allowed to reanneal under conditions where the anti-parallel mutant strands and nearly identical wild type strands will form heteroduplexes containing one wild type strand and one mutant strand. The term "nearly identical", as used herein, is defined as including sequence changes of up to approximately 25 base pairs from a previously existing nucleic acid sequence. Because the ratio of wild type to mutant sequence is high, essentially all single-stranded mutant sequences will reassociate with wild type sequences. Importantly, the melting temperature of each such heteroduplex is significantly lower than that of the perfectly matched wild type homoduplex. Thus, essentially all mutant DNA sequences are converted to a form (heteroduplex) easily separated from the predominant wild type (homoduplex) DNA sequence using the method described herein.

Briefly, the present method includes the following steps. The DNA of interest (i.e., the DNA to be analyzed in the present method) is typically a DNA sequence of approximately 100–500 base pairs from a biological source that is suspected of containing a mutation, or mutations of interest. The DNA of interest is then isolated from the biological source, such as cells, viruses, body tissues and fluids, plasmids, environmental samples or experimental mixtures. Isolation renders the DNA of interest substantially free of other cellular macromolecules, such as proteins. Isolation can be accomplished using known laboratory techniques.

The melting temperature of the DNA of interest can be calculated (if it is not known a priori) to determine if the DNA contains two iso-melting domains, a first iso-melting domain, referred to as a low temperature iso-melting domain which melts at a first melting temperature, and a second iso-melting domain, referred to as a high temperature iso-melting domain, which melts at a second, higher temperature. Alternatively, the melting temperature of the DNA can be determined experimentally.

The mutation of interest must lie within a suitable low temperature iso-melting domain, that is, an iso-melting domain contiguous with an iso-melting domain of higher thermal stability. In addition, the low-temperature iso-melting domain must be of suitable length (e.g., a length of approximately 100–150 base pairs). If the mutation of interest does not lie within such an iso-melting domain, the DNA of interest can be modified to attach contiguous high and/or low iso-melting domain/domains, thus, converting the iso-melting domain containing the mutation to a suitable low temperature melting domain. Modification of the DNA can be accomplished by various methods. For example, a high temperature clamp sequence can be attached to the DNA of interest by reaction with DNA ligase. Alternatively a clamp can be attached by amplifying the sequence of interest by suitable amplification means (i.e., amplification methods with low error rates such as high fidelity PRC) using as one DNA primer an iso-melting sequence which contains a sequence of higher thermal stability. The sequence modification can also be accomplished by melting and reannealing the DNA of interest, as described below, with a molar excess of a previously synthesized DNA sequence containing the desired sequence in the 5' direction which contains a sequence of higher thermal stability. This reaction results in DNA comprised of two strands of uneven length (i.e., one strand is shorter than the other strand). The shorter DNA strand can then be extended by action of DNA polymerase to create a double stranded molecule comprising two strands of the same length.

The isolated, double-stranded DNA sequence of interest, containing the two iso-melting domains, can be further processed in such a manner as to make it accessible to restriction endonucleases, or other agents, capable of cutting the DNA in a sequence-specific manner. The isolated DNA is then cut with one or more appropriately-selected restriction endonucleases, or other sequence-specific agents, to produce double-stranded (ds) non-mutant/non-mutant and mutant/mutant DNA fragments. The resulting DNA fragments can be processed as obtained, or can optionally be partially isolated to remove some of the undesirable fragments, or to obtain fragments of a specified length, thereby resulting in the enrichment of the fragmented double-stranded DNA of interest. The partial isolation is based on size separation, such as, for example, by PAGE, capillary electrophoresis with sieving matrix, or other well-known laboratory techniques. It is important to note that the DNA sequences analyzed by the method described herein, can be of the same length, or of different lengths and can differ as little as one base pair in the nucleotide sequence.

The dsDNA fragments are melted by heating (denatured) and cooled (reannealed) under controlled conditions to allow non-mutant sequences and mutant sequences to form non-mutant/mutant heteroduplexes. Also formed upon reannealing, are homoduplexes containing non-mutant/non-mutant strands, as well as, homoduplexes containing mutant/mutant strands. The step of converting mutant/mutant homoduplexes to non-mutant/mutant heteroduplexes may follow or precede the fragmenting step. Some DNA of interest can be naturally obtained in a form such that experimental manipulation to form heteroduplexes is unnecessary. This is particularly true when "mutant" DNA describes DNA with chemical alterations.

The heteroduplexes are then separated from homoduplexes within a polymer matrix using partially denaturing conditions which result in partial melting of the non-mutant/ mutant heteroduplexes, without melting the non-mutant/non-mutant homoduplexes. The heteroduplexes, upon partial melting, migrate at a slower velocity through the polymer matrix than the unmelted homoduplexes.

The polymer matrix is contained within a channel, or conduit, comprised of a material suitable for use in a high electric field. In one embodiment, the channel is a capillary column. These channels can be arranged in arrays, permitting high throughput by the simultaneous analysis of multiple samples. (When using a capillary column and constant denaturing conditions, the method described herein is also referred to as constant denaturant capillary electrophoresis, or CDCE.)

Importantly, in one embodiment of the present method, the polymer matrix is formulated to be "replaceable", that is, easily removed (extracted or extruded) from the channel after a sample run, allowing fresh polymer matrix to be introduced into the channel prior to the next sample run. Thus subsequent cycles of CDCE can be easily performed. Each cycle can include subjecting a sample to CDCE, collecting the fractions containing the separated heteroduplexes, optionally amplifying the fraction by suitable amplification means, replacing the polymer matrix, and again subjecting heteroduplexes to CDCE. Each cycle of CDCE can significantly improve the detection of mutant DNA.

In another embodiment, the channel can be a groove, or canal, cut into a small plate, or chip. Each chip can contain single or multiple channels, thus also permitting analysis of multiple samples.

The method of separation and analysis described herein is performed under partially denaturing conditions which result in the melting of the low temperature iso-melting domain, but not the high temperature iso-melting domain. In one embodiment, the partially denaturing conditions appropriate for each mutant DNA sequence of interest are achieved by a combination of temperature of the polymer matrix contained within the channel and concentration of chemical denaturant (e.g., urea and/or formamide) contained within the polymer matrix. In another embodiment, the appropriate partial denaturing conditions are achieved by temperature of the polymer matrix alone. For example, a denaturing condition can be achieved by a temperature moderately above ambient temperature (e.g., the surrounding temperature, or room temperature) and a moderate concentration of a chemical denaturant in the polymer matrix. Alternatively, a lower temperature can be used if the concentration of chemical denaturant in the polymer matrix is increased. Denaturing conditions can also be achieved by temperature alone, without the presence of chemical denaturants in the polymer matrix. In this embodiment, the temperature selected to achieve the denaturing condition is the temperature at which, or close to the temperature at which, the lower temperature iso-melting domain of the non-mutant/non-mutant homoduplex melts. Generally, in the method described herein, the temperature of the polymer matrix is from approximately 24° C. to approximately 100° C. However, certain DNA sequences may require slightly higher or slightly lower temperature to achieve partial melting, depending on the nucleotide sequence of interest. In either embodiment, the partially denaturing conditions can be constant or achieved by a gradient.

The polymer matrix is subjected to a high electrical field (e.g., from approximately 50 to approximately 1200 volts/cm) for a period of time sufficient to separate the heteroduplexes from homoduplexes in the matrix. The relative movement of the duplexes can be detected as they migrate through the matrix and pass a detector located at a fixed point. Alternatively, the movement of duplexes through the matrix can be stopped at a specific time by cessation of the electric field, or by achieving a particular condition in the polymer matrix which impedes the movement of the duplex, essentially "fixing" the duplex in the matrix. The relative positions of the arrested duplexes can then be determined by scanning the matrix. Finally, the relative movement of duplexes can be detected by monitoring the flow-through solution (i.e., eluate) which contains the heteroduplexes and homoduplexes as it exits from the matrix. (This profile of the relative positions of the duplexes within the polymer matrix, or as they exit the matrix is referred to herein as an electropherogram.) In any case, the relative mobility of the heteroduplexes and homoduplexes through the matrix is dictated by the cooperative equilibria of the iso-melting domains of the DNA fragments under the specified partially denaturing conditions.

Detection (or recording) of the movement of the duplexes through the matrix can be accomplished by a variety of means, including radioactive, fluorescent or chemiluminescent means. In particular, detection by the use of laser-induced fluorescence (LIF) is convenient and permits high sensitivity detection. Fractions of the eluate may also be collected as they exit from the channel. The collected fractions may be analyzed by known sequencing techniques, with or without amplification, to determine the nucleic acid sequence of the DNA contained in the collected fractions. Alternatively, fractions can be collected and the heteroduplex-containing fraction passed through the polymer matrix multiple times as a means to enrich the heteroduplex-containing fraction relative to the wild type DNA fraction, and thus, enhance detection of the mutation of interest.

An important advantage to the method of separation and detection described herein is the use of thin polymer matrices which allow rapid dissipation of heat, and development of low current, thus permitting the use of a high electrical field. Use of a high electrical field effects separation of mutant and wild type DNA sequence in a shorter time period than is possible through the use of conventional denaturing gel electrophoresis. Moreover, the use of non-cross-linked polymer matrices, containing low concentrations of chemical denaturants, or no chemical denaturants, to decrease the viscosity levels permits replacement of the matrix after each run, which greatly enhances reproducibility and ease of operation.

For a typical 100–200 base pair (bp) DNA fragment, mutant-containing heteroduplexes are separated from wild type homoduplex sequences in generally less than 30 minutes. An advantage of the method described herein is that DNA sequences of interest can contain the same number of base pairs (e.g., the sequences are of the same length). Another advantage of the method described herein is the ability to detect a DNA sequence of interest which represents only a small fraction of the total DNA sequences in the sample. In particular, this method permits detection of mutant DNA molecules representing only a small fraction of the total number of DNA molecules present in a sample. For example, a fraction of mutant DNA molecules representing as low as $3\times10^{-4}$ of the total mixture of mutant and wild type molecules run on a capillary column as described herein, can be detected. Thus, a capillary column containing polymer matrix, run under the constant denaturing conditions described herein, is not saturated with $10^{10}$–$10^{11}$ molecules per peak, and a peak with as few as $3\times10^{4}$ copies of dsDNA is visible above background using LIF. Also as described herein, this fraction of mutant DNA molecules can be enriched by subsequent cycles of CDCE so that even a smaller fraction of mutant molecules (e.g., $5\times10^{-6}$) can be detected.

The method described herein provides a fast and reproducible procedure to separate and detect mutant DNA sequences from wild type sequences when the mutant sequences represent only a small fraction of the total DNA contained in the sample. The separation method of the present invention is well-suited for any biotechnological application where detection of mutant sequences is important. This method is especially well-suited for detection of point mutations in a DNA sequence, mutations in plasmids and nucleic acid sequences to be used in gene therapy, mutational spectrometry (e.g., the determination of the type and number of mutations for a given sequence, such as the p53 tumor suppressor gene), or for the simultaneous screening of pooled human tissue samples for detection of polymorphisms or germinal mutations.

BRIEF DESCRIPTION OF THE DRAWING

FIG. 1B is a schematic diagram representing the HPRT exon 3 melting map and the relative positions of the oligonucleotide primers used in the amplification protocol.

FIG. 1A is a schematic representation of the PCR strategy of HPRT exon 3.

DETAILED DESCRIPTION OF THE INVENTION

Figure 2:
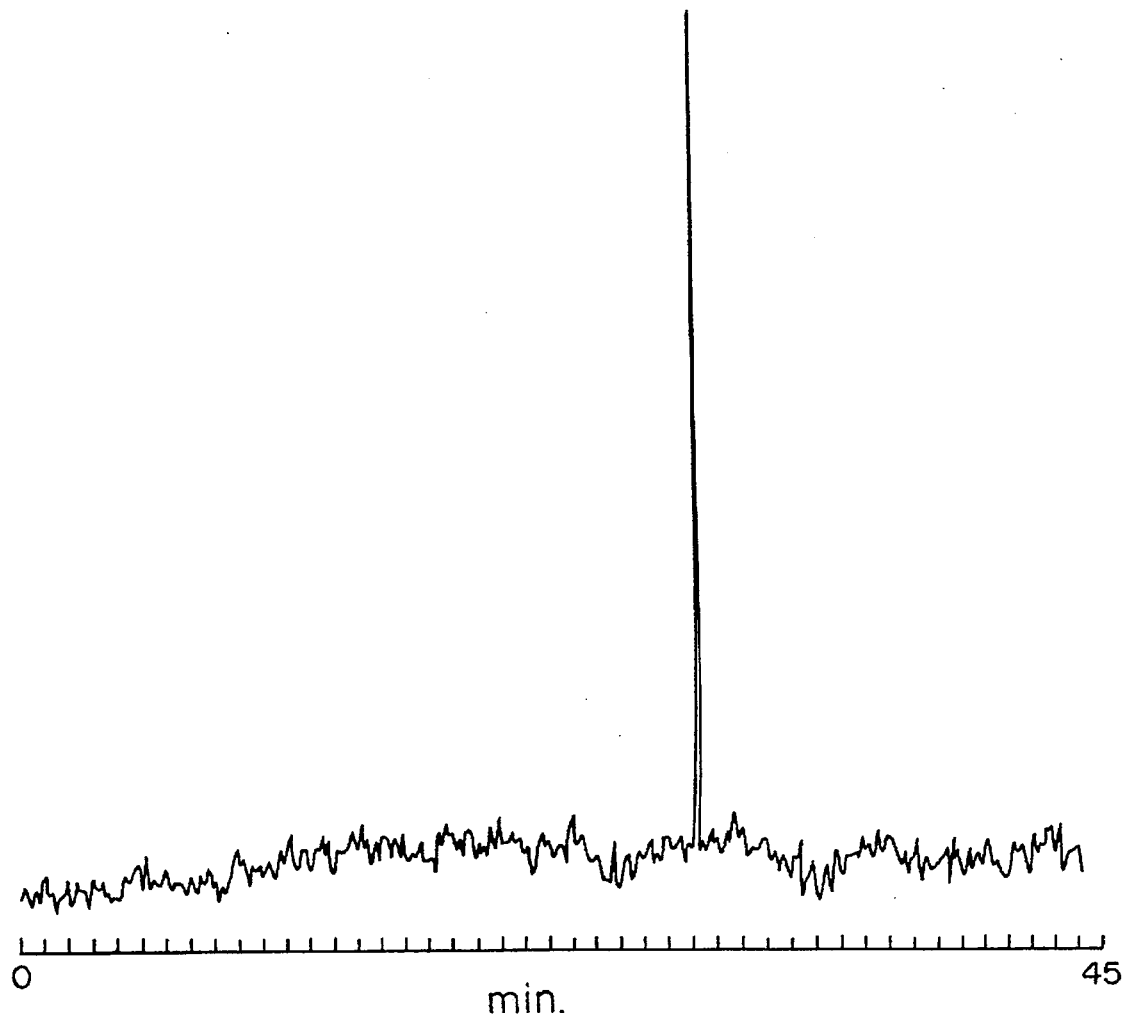
FIG. 2 is a capillary electropherogram showing the DNA banding profile of a wild type HPRT exon 3 fragment using 7% monomer linear polyacrylamide in 7M urea at room temperature. Only one peak, the non-mutant/non-mutant homoduplex is observed.

The present invention relates to a method of separating, or resolving, mutant nucleic acid sequences from non-mutant nucleic acid sequences, enriching the fraction of mutant DNA relative to the total DNA contained in a sample, and to methods of detecting point mutations, or determining a mutational spectrum, or a profile of mutations, present in nucleic acid sequences from a biological sample. The biological sample can be from any source containing nucleic acids, especially tissue or body fluid containing cells, such as blood, urine, cerebral spinal fluid, lymph node tissue and sputum, plasmids, recombinant nucleic acids, agricultural sources, such as recombinant plants, or any synthetic nucleic acid sequence. In particular, the method described herein is useful for separating and identifying selected mutant DNA sequences from a complex population of DNA molecules which contain the selected, or target mutant DNA sequence (i.e., the sequence of interest), mutant DNA sequences other than the selected mutant DNA sequences and non-mutant (also referred to herein as wild type) DNA sequences. Thus, using the denaturing conditions, polymer matrices, and high electrical field as described herein, it is possible to separate DNA sequences that contain difference in a single base pair, or differences in several base pairs (e.g., wherein the term "several" can include as many as 25 base pairs) in a DNA iso-melting sequence of approximately 100–200 base pairs quickly and reproducibly.

Moreover, the method described herein provides the means to separate mutant DNA sequences from wild type DNA sequences when the mutant sequence represents only a small fraction of the total DNA present in the sample. Furthermore, modification of the method described herein can reasonably result in the detection of most mutations in DNA iso-melting sequences of up to approximately 1000 base pairs in length. As defined herein, a mutant nucleic acid sequence is a sequence which differs by one or more nucleotides from the corresponding wild type (non-mutant or unaltered) sequence. These differences include nucleotide modifications, deletions, substitutions or insertions. The nucleic acid sequence can be a DNA or RNA sequence. A mutant nucleic acid sequence is also a sequence containing chemically altered base pairs, such as with naturally methylated DNA or DNA reacted with chemical carcinogens.

A sample of DNA to be analyzed for the presence of a mutant sequence of interest, or mutant sequences of interest, is obtained, using known techniques, from a tissue, body fluid or other sample (e.g., bacterium, virus, other microorganism or plasmid) containing cells. The number of cells needed for analysis is dependent on the particular application (particular mutation(s) to be detected) and the numbers of copies of the DNA sequence of interest to be analyzed that are present per cell. The DNA of interest is isolated by standard laboratory techniques to obtain isolated DNA free from proteins, carbohydrates, fats and RNA (or RNA free from DNA).

The method described herein can be used to separate double-stranded DNA sequences having both a high temperature iso-melting domain and a low temperature iso-melting domain. An iso-melting domain is a domain in which all base pairs melt essentially simultaneously so that the sequence is either fully annealed or fully melted. A cooperative equilibrium exists between the fully melted and unmelted domains. DNA sequences suitable for separation by the method described herein will contain two iso-melting domains in which the "higher" melting temperature domain melts at a temperature approximately 5° C. higher than the melting temperature of the "lower" temperature melting domain. The low melting temperature domain will be contiguous with the high temperature melting domain.

The melting characteristics of a given DNA sequence can be determined by known computational methods. For example, the melting temperatures of specific domains of a DNA sequence can be calculated using an algorithm developed by Fischer and Lerman (Fischer, S. G., and Lerman, L. S., *Proc. Natl. Acad. Sci. USA* 80:1579–1583 (1983); Lerman, L. S. and Silverstein, K., *Meth. Enzymol.* 155:482–501 (1987)). This algorithm predicts the melting temperature of DNA based solely on its nucleotide sequence. For example, the melting map for exon 3 of human hypoxanthine guanine phosphoribosyl transferase (HRPT), calculated by the Fischer and Lerman method, is shown in FIG. 1A. Note that the DNA sequence is organized into melting domains of a few hundred base pairs. Alternatively, conditions required to melt the low temperature iso-melting domain can be determined experimentally using the method described herein. Aliquots of the DNA sample of interest can be run under various denaturing conditions to determine which conditions result in the melting of the domains contained within the sequence.

Thus, DNA suitable for separation in the present method will contain two contiguous iso-melting domains. The first iso-melting domain is referred to herein as the low temperature iso-melting domain, and a second iso-melting domain is referred to herein as the high temperature iso-melting domain (i.e., a domain of higher thermal stability than the first iso-melting domain). The mutation of interest must lie in the low temperature melting domain, contiguous with a domain of higher thermal stability. However, if a high temperature melting domain is not found contiguous with the domain containing the mutation in the naturally occurring DNA molecule, a variety of techniques can be employed to incorporate a domain of higher thermal stability at an appropriate position, thus, essentially converting the domain containing the mutation of interest into a low temperature melting domain contiguous with a high temperature melting domain.

For example, a "clamp" of double-stranded DNA sequence of a higher thermal stability (i.e., a higher melting temperature) can be attached to the DNA sequence of interest by methods well-known in the art. (Cariello, N. F., et al., *Am. J. Hum. Genet.*, 42:726–734 (1988)). The synthetic clamp sequence must be a non-monotonic nucleic acid sequence. (For example, a nucleic acid sequence consisting of only the base guanine (G) and its complementary strand would not be suitable as a clamp.) The attachment of the clamp sequence can be accomplished by ligating the synthetic higher temperature melting domain to the sequence of interest by known methods of DNA ligation. Alternatively, a higher temperature melting domain can be attached by forming heteroduplexes as described below, with synthetically created wild type sequence neighboring a high temperature melting domain and extending the mutant DNA strand of the heteroduplex into a higher temperature melting domain with DNA polymerase.

At times, the DNA of interest will not contain a suitable iso-melting domain. For example, the preferred length of the low-temperature iso-melting domain is approximately 100 to approximately 150 base pairs. If the DNA sequence of interest is less than 100 base pairs long it may be necessary to attach additional sequence to obtain a suitable iso-melting domain. The DNA sequence of interest can then be modified to attach not only a domain of higher thermal stability to one end of the sequence of interest, but, to the other end of the sequence, a domain which melts at a temperature at, or near, the melting temperature of the naturally occurring DNA sequence of interest. This approach can be used to create a suitable low temperature iso-melting domain as well. This can also be accomplished as described above for attaching a high temperature iso-melting domain.

The isolated DNA is processed to produce double-stranded DNA in a form suitable for separation in the present method. Specifically, the DNA is cut into fragments of suitable size, or length, for separation. The length of the low temperature iso-melting domain in fragmented DNA suitable for use in the present method is typically less than 1000 base pairs long, preferably between 75 and 200 base pairs long, and most preferably between 75 and 125 base pairs long. The optimal size of the DNA fragment to be analyzed will also depend on the location of the mutation within the molecule. Double-stranded DNA fragments of specified length can be generated by a variety of methods including, for example, fragmentation, or digestion, to obtain fragments of a defined length. Importantly, the method described herein can separate mutant and wild type DNA sequences even though the sequences are of the same length. Generally, fragmentation is accomplished by cutting with a selected restriction endonuclease(s) or other chemical agent which can recognizably cut DNA in a sequence-specific manner. The restriction endonuclease, or other agent, is chosen to cut the DNA sequence in such a manner that the mutation of interest is contained within the DNA fragment of the desired length.

This fragmentation step results in many different DNA fragments of various lengths. Partial isolation of DNA fragments of interest can be accomplished by a variety of standard techniques, such as PAGE or other means of size separation. The partial isolation can result in removing the bulk of fragmented DNA, and simplify subsequent DNA processing, e.g., DNA amplification. The double-stranded DNA fragments generated in this step can also be labeled with a detectable reporter group, such as fluorescein, an infrared dye, or a radioactive material, using well known techniques.

Before separation of DNA fragments, specifically separation of mutant DNA from wild type DNA sequences, the double-stranded mutant DNA sequences are converted to heteroduplex molecules, containing one wild type DNA strand and one anti-parallel mutant DNA strand. This conversion step may precede the fragmentation step, or may follow the fragmentation step. In either case, the conversion to heteroduplexes is carried out by heating the DNA sequences in the sample resulting in melting (separation into two strands) of the double-stranded DNA, and cooling the sample to allow reannealing of the strands to form duplexes. (See, for example, U.S. Pat. No. 5,045,450, the teachings of which are incorporated herein by reference.) During the melting/reannealing process, non-mutant DNA sequences form complexes with mutant DNA sequences, referred to herein as a heteroduplex. Homoduplexes containing mutant/mutant strands and non-mutant/non-mutant strands are also formed.

To ensure that mutant DNA sequences will form heteroduplexes, an excess of wild type sequence must be present in the sample. In most samples to be analyzed by the present method, wild type DNA represents a 10–10,000,000-fold excess over mutant DNA sequences. Thus, the conversion step can be carried out without the need for additional manipulation of the sample. In those instances in which excess wild type sequence is not present, addition of wild type sequence to form an excess prior to conversion may be necessary to ensure that a molar excess ($\geq 10\times$) of wild type sequences is present. The presence of a molar excess of wild type sequence in the sample significantly reduces formation of mutant/mutant homoduplexes. Thus, by heating a sample mixture containing a predominance of wild type DNA sequences admixed with mutant DNA sequences, by mass action, a significant portion of mutant homoduplexes are converted to heteroduplexes containing one mutant and one wild type strand. It is important to note that some DNA suitable for analysis in the present method is obtained in a natural state that does not require the formation of heteroduplexes prior to analysis in the present method.

Importantly, the melting temperature of each heteroduplex is characteristic of that particular heteroduplex, and significantly lower than that of the perfectly matched wild type homoduplex. The heteroduplex, under specified conditions, will partially melt, forming a molecule that will migrate at a slower velocity than the unmelted, perfectly matched homoduplex. Thus, the mutants are converted to a form easily separated from the predominant wild type form. The wild type DNA sequences used in this step can be labeled with a detectable probe, such as fluorescein, to form labeled duplexes, which facilitates subsequent detection.

Mutant-containing heteroduplex molecules are then separated from homoduplex molecules by the method described herein. An aliquot of the sample containing a mixture of wild type/mutant heteroduplexes, wild type/wild type homoduplexes, and other DNA sequences remaining from the original sample is applied to a channel containing a polymer matrix. The method of introduction can be by electro-injection, physical application, or other means for applying a sample, for example, to an electrophoretic apparatus. The polymer matrix is contained within a channel. The channel must be suitable for use in a high electric field. For example, if the channel is a capillary column, the capillary is typically a fused silica tube having a small diameter bore (e.g., a diameter of about 10 to 400 microns, or more preferably, 50–200 microns). The interior of the capillary is coated with a neutral coating material to decrease the charge of the fused silica to a negligible extent. The coating (e.g., organosilane) can be adsorbed or covalently bound to the channel walls. Capillary columns suitable for use in the present method are discussed in U.S. Pat. No. 5,112,460, the teachings of which are herein incorporated by reference. Although capillary columns are preferred for the method of separation described herein, slabs may also be used in this method. Slabs should be thin, having a thickness of approximately 10–400 microns, preferably 50–200 microns.

The separation method of the present invention can also be adapted for use on a small plate, or a "chip", or a series of "chips". For example, channels can be etched, or cut, into the chip and filled with the polymer matrix, the sample applied and electrophoretically run under conditions sufficient to achieve separation of wild type homoduplexes from wild type/mutant heteroduplexes with the same resolution of full-size capillary column separation. Moreover, the chips are easily disposed of, and a new chip can be used for each separation.

The polymer matrix is generally polyacrylamide. However, other polymer matrices can be used, such as methyl cellulose, dextran or polyethylene glycol (PEG) (See, for example, Ganzler, K., et al., *Anal. Chem.* 64:2665–2671 (1992). In a preferred embodiment of the present method, the polymer matrix is "replaceable". That is, prior to each loading of sample aliquot on the polymer matrix contained in the channel, the depleted matrix is removed, typically by blowing out the old matrix, and fresh matrix is introduced. The ability to replace the polymer matrix in the channel for each run is important to the reproducibility of the present separation method. After a sample is run through the matrix, its ionic strength may be altered, resulting in alterations in the conductivity of the matrix. Exposure to high temperature can also be destructive to the matrix. Blowing out the depleted matrix from the channel, and introducing fresh matrix for each sample run assures reproducible denaturing conditions. Alternatively, if a chip is used, the chip may be disposed of after each run.

A polyacrylamide matrix generally has a monomer concentration of 15% or less. Preferably, a concentration of 7% or less is used in the present method, and more preferably, the concentration is between 4–6% for replaceable polymer matrices. Bis acrylamide cross-linker, or other suitable cross-linker, is omitted, or included only in very low concentration. Preferably, for replaceable polymer matrices, the matrix is linear polyacrylamide. The sample introduced into the polymer matrix must be introduced under conditions that allow initial movement of the sample into the matrix without melting of the duplexes.

Separation of DNA heteroduplexes from DNA homoduplexes begins by subjecting the channel to a high electrical field through which the negatively charged DNA moves, or migrates, through the polymer matrix toward the positively charged anode at the opposite end of the channel. The field strength can vary depending on the conditions of the separation. For example, when the channel is a capillary column, an electrical field of 1200 volts/cm. or more can be used in this method. Typically, the field strength is between 50 and 1200 volts/cm., and preferably the field is between 100–500 volts/cm. Once the electrical field is applied, if the sample has lower conductivity than the conductivity of the column, the DNA in the sample aliquot becomes "focussed", or condensed, into a very small volume at the top of the channel. Focussing of the DNA sample is an important factor to the high resolution achieved by this method. At this point of the separation method, all duplexes are moving through the matrix at the same, or nearly the same, velocity. Preferably, this velocity is approximately 1–2 cm/min.

A short distance from the beginning of the polymer matrix, the migrating duplexes enter into a portion of the channel termed the "denaturing zone". The denaturing zone comprises a portion of the channel in which the conditions cause the heteroduplexes to partially denature while the homoduplexes remain intact. The partially denatured heteroduplexes are slowed in their movement through the matrix. Thus, once the wild type homoduplexes and wild type/mutant heteroduplexes enter this denaturing zone, their velocities become distinct. That is, the velocity of the wild type homoduplex, in the denaturing zone, is greater than the velocity of the wild type/mutant heteroduplex. For example, as the duplex molecules migrate into the denaturing zone, the heteroduplex molecules, which contain at least one mismatched base pair, melt at a denaturing condition different than that at which the wild type homoduplex molecules melt. Thus, the conditions of the denaturing zone are such that the wild type homoduplex will migrate at a faster velocity than the wild type/mutant heteroduplex and the wild type homoduplexes can be separated as to relative position in the denaturant zone from the wild type mutant heteroduplexes.

The denaturing zone conditions to be used in the method will depend on the melting characteristics of the DNA of interest. In particular, the conditions within the denaturing zone must result in partial denaturation of the heteroduplex DNA molecules, specifically the low temperature isomelting domain. The partial denaturing conditions can be constant throughout the zone, or discontinuous (e.g., a temperature gradient or chemical denaturant gradient formed within the polymer matrix). The partial denaturing conditions are achieved by temperature or a combination of temperature and chemical denaturants contained in the polymer matrix within the zone. Typically, the temperature is elevated temperature (as used herein, elevated temperature means temperature above ambient temperature). For example, if ambient temperature is approximately 22° C. (about 72° F.) then elevated temperatures would run approximately 24° C. and above. The method can be carried out at ambient temperature if chemical denaturant is present in the polymer matrix. Generally, elevated temperature will result in rapid movement through the matrix without unwanted chemical reactions occurring within the polymer matrix. However, if chemical denaturant is present, the temperature may be lowered to slow the movement through the matrix. The optimal combination of temperature and chemical denaturant will vary for each sequence of interest. These conditions may be determined experimentally by trial assays of the DNA of interest in the present method varying the partially denaturing conditions.

The temperature of a capillary column can be elevated above ambient temperature by a water jacket, heating block, or other appropriate means, surrounding a portion of the capillary. Generally, the beginning portion and opposite end portion of the column are not included in the denaturing zone. For example, a 10 cm portion of a capillary is heated where the effective length of the capillary (injection to on-column detection point) is 18 cm. Other conventional methods of controlled heat, such as lamps or hot air, can also be used.

The temperature chosen will depend upon the melting characteristics of the DNA sequence of interest and the amount and type of chemical denaturant, if any, present in the polymer matrix. In general, the temperature range is above-ambient temperature, (e.g., between approximately 24° C. and approximately 100° C.). If chemical denaturant is present in the matrix, the temperature used may be closer to ambient temperature. If chemical denaturant is not present in the matrix, elevated temperature alone can achieve the desired denaturing condition. The optimal temperature can be determined empirically for each sequence of interest. For example, if the melting temperature of the DNA sequence of interest is 63° C., an initial run may be performed at 60° C., a second run at 61° C., and so forth until the optimal temperature to achieve the desired partial denaturing conditions is determined as observed from the electropherogram. Thus, if the temperature is set at a few degrees above the melting temperature of the wild type/mutant heteroduplex, the wild type homoduplex will proceed through the column at close to maximum velocity in its unmelted state, whereas the wild type/mutant heteroduplex, which has lower thermal stability, will partially melt resulting in a slowed mobility through the zone. The channel regions outside the denaturing zone are such that all double-stranded DNA species are unmelted and migrate at a constant velocity. Thus, while moving through the denaturing zone, wild type/mutant heteroduplexes in the partially melted state, move at a slower velocity than the unmelted wild type/wild type homoduplexes resulting in separation of heteroduplexes from homoduplexes.

Typically, chemical denaturants such as formamide and urea, either alone or in combination, are used. However, other standard chemical denaturants that tend to melt double stranded DNA can be used in the present invention, including e.g., dimethyl sulfoxide (DMSO). The most appropriate chemical denaturant and its most appropriate concentration may vary depending on the DNA sequence of interest. The concentration of chemical denaturant can be constant throughout the denaturant zone, or in gradient concentration, ranging from, for example, a low concentration at the beginning of the zone, to a higher concentration at the end of the zone. The most appropriate chemical denaturant and its appropriate concentration can be determined.

In one embodiment of the present invention, the partial denaturing conditions in the polymer matrix are constant. Using a capillary column under constant denaturing conditions is referred to herein as constant denaturing capillary electrophoresis or CDCE. In another embodiment of the present invention, gradient denaturing conditions can be used to achieve separation and detection of mutant sequences. A gradient (either chemical or temperature) can separate multiple heteroduplexes from homoduplexes contained in a sample in a single assay. Thus, a gradient can be used for rapid determination of constant denaturing conditions to be used in further analysis. Gradient denaturing conditions are also desirable if multiple sequences with different melting characteristics are to be analyzed. Moreover, gradient denaturing conditions can be used as a method to "fix" the duplexes in the polymer matrix for the purpose of scanning the matrix to determine the relative positions of the duplexes. For example, the migrating duplexes will move through the matrix and at certain points the denaturing conditions will change such that migration will stop and the duplex will become fixed in the matrix. Subsequently, the matrix can be scanned to determine the relative positions of the duplexes in the matrix. Standards with known melting characteristics can be used to calibrate the matrix.

Detection of the separated wild type homoduplexes and wild type/mutant heteroduplexes can be accomplished in a number of ways, including monitoring the movement of the duplexes through the matrix, or the exit of the duplexes from the matrix, or stopping the movement of the duplexes in their relative positions on the channel by shutting off the electrical field at a specified time and scanning the matrix. In particular, capillary electrophoresis offers a significant advantage with regard to on-line detection of a small number of heteroduplex molecules. (Karger, B. L., et al., *J. Chromatog.* 492:585–614 (1989)). Suitable on-line methods are analogous to detection methods developed for high pressure liquid chromatography (HPLC). For example, DNA fragments can be labeled by conventional methods with a fluorescent compound, or near infra red dye, prior to separation. Many such compounds are known to those skilled in the art, fluorescein being a commonly used member of this class of compounds.

At any convenient point beyond the denaturing zone of the channel (the terminus remote from the loading point of the channel) is located a light source (e.g., an argon laser) and a detector (e.g., a photomultiplier tube). The laser is tuned to a wavelength known to cause fluorescence of a fluorescent compound and oriented so that the light passes through the channel and is directed to the detector. As the fluorescently labeled compound passes through the argon laser beam, the fluorescent compound is excited and its fluorescence is detected by the detector. The detector feeds the data to a control unit via an analog-digital interface. The data is then plotted as an electropherogram (i.e., an elution, or migration profile) by a recorder.

In one embodiment of the present invention, a laser-induced fluorescence (LIF) detection device is used to monitor the homoduplexes and heteroduplexes migrating through the matrix, thus producing electropherograms. The channel can be calibrated by running known samples containing heteroduplexes and/or homoduplexes. The electropherograms of unknown samples can then be compared with the standardized electropherograms to identify heteroduplexes and homoduplexes of interest.

In addition to the spectroscopic approach described above, other detection methods have also been developed. Conductivity has been successfully utilized by Huang et al. (*J. Chromatog.*, 458:303 (1988)). This detector can prove useful for small ions which are highly conductive. Electrochemical detectors can also be employed using an approach developed by Wallingford and Ewing (*Anal. Chem.* 59:1762 (1987)). A third detector type development is a radioactivity detector (see e.g., Gordon et al., *Science* 242:224 (1988)).

Another detector which is useful in combination with capillary electrophoresis is the mass spectrometer. (Smith et al., *Anal. Chem.* 60:1948 (1988)); (Lee et al., *J. Chromatogr.* 458:313 (1988)).

Other conventional methods can also be used to analyze the separated DNA heteroduplexes and DNA homoduplexes. For example, individual fractions containing separated duplexes can be collected as they exit the polymer matrix. These fractions can then be subjected to remote detectors such as absorption of ultraviolet light detectors in certain cases (e.g., when exposure to UV light would not compromise the accuracy of analysis) and scintillation counters. Alternatively, these collected fractions can amplified (e.g., by cloning or high fidelity PCR as described in U.S. Ser. No. 07/999,179, the teachings of which are incorporated herein by reference), if necessary, and sequenced using standard techniques to determine the precise nucleic acid sequence of the duplexes contained in the fractions. Alternatively, the distal tip of a capillary can be contacted with a moving membrane so that the flow-through produces a linear track on the membrane. The membrane can then be subjected to conventional analysis, such as staining or autoradiography.

In one embodiment of the present invention, the polymer matrix is a replaceable matrix, which can be easily removed from the channel after the first separation run. Thus, after the fractions containing the DNA duplexes of interest are collected as they exit from the matrix, the old matrix is blown out and replaced with fresh matrix. The collected fraction, or collected pooled fractions, containing the heteroduplexes, can be optionally amplified by a suitable low-error amplification method, and then reintroduced into the fresh polymer matrix and again subjected to the high electrical field under the identical partially denaturing conditions, or under altered conditions, as described above. For example, a two hundred-fold enrichment of mutant DNA has been achieved with an additional cycle. The fraction, or fractions, containing the heteroduplexes can again be collected, optionally amplified, and sequenced to determine the DNA sequence of the heteroduplexes. This separation step results in enrichment of the heteroduplexes in the collected fractions, thus facilitating analysis of the mutation of interest.

The method of separating wild type homoduplexes from wild type/mutant heteroduplexes described herein, provides a reproducible means of efficiently removing wild type DNA sequences from a DNA sample containing mutant DNA sequences of interest, thus, enriching the mutant-containing fraction. For example, a typical analysis of a DNA sequence of interest can be accomplished at present, in approximately 7.5 hours. Further optimization of the method described herein can reasonably reduce this time even more. Furthermore, the method described herein can be easily automated, which permits the rapid processing of samples, or a series of samples.

The human hypoxanthine guanine phosphoribosyl transferase (HPRT) gene is a suitable model for the study of detecting point mutations in human cells by the separation method described herein. The HPRT gene spans approximately 44 kb in genomic DNA and is split into 9 exons. Exon 3 contains the largest continuous portion of the coding frame (28%). The exon contains an 80 base pair (bp) high temperature iso-melting domain adjacent to a 104 bp low temperature iso-melting domain, which are shown schematically in FIG. 1A.

In addition, a mutant of the HPRT gene which is responsible for a form of gout has been identified and sequenced. The mutant allele has been designated HPRT-Munich. This mutant allele contains a GC to TA transversion at base pair 312 in the low temperature melting domain of exon 3, 7 base pairs from the 3' end of the exon. In other words, the wild type (wt) and the mutant (mu) are 184 bp dsDNA molecules which differ by only a single CG to AT transversion in the low temperature melting domain at the 7th position from the 3' end of the exon. (Cariello, N. F., et al., *Am. J. Hum. Genet.*, 42:726–734 (1988)).

Wild type HPRT exon 3 and HPRT-Munich exon 3 were amplified from isolated genomic DNA as described in detail in Example 1. The individual amplification products were purified by PAGE and DGGE, also as described in Example 1. Prior to loading the DNA fragments on the gel, the fragments were mixed to permit formation of heteroduplexes which contain wild type/mutant DNA sequences. The reannealed product was subjected to DGGE and the separated heteroduplexes and homoduplexes were isolated from the gel and diluted to a concentration of about $10^8$ copies per microliter.

Wild type HPRT exon 3 DNA alone was first run on the capillary electrophoresis system described in Example 1 at room temperature. At room temperature, the low temperature melting domain of the wild type fragment does not melt when run on a denaturing polymer matrix containing 7M urea. As can be seen in FIG. 2, the wild type duplex DNA passed the laser-induced fluorescent (LIF) detector as a single peak at between 27 and 28 minutes.

Figure 3:
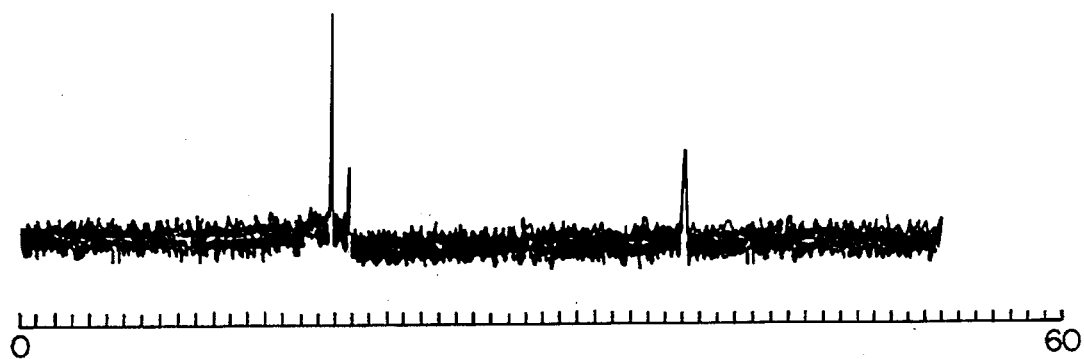
FIG. 3 is a capillary electropherogram showing the DNA banding profile of a wild type HPRT exon 3 fragment using 7% monomer linear polyacrylamide in 7M urea at 60° C. Some of the homoduplex has been fully melted, including the high melting domain. This creates a single-stranded DNA of greater velocity in electrophoresis.

FIG. 3 shows the electropherogram with wild type sequence alone at an elevated temperature of 60° C., (approximately $10^8$ copies in water). An early peak at between 17 and 18 minutes post-injection is believed to represent single-stranded DNA. A second peak, present at between 38 and 39 minutes post-injection, is believed to represent the partially denatured, partially duplex structure.

Figure 4:
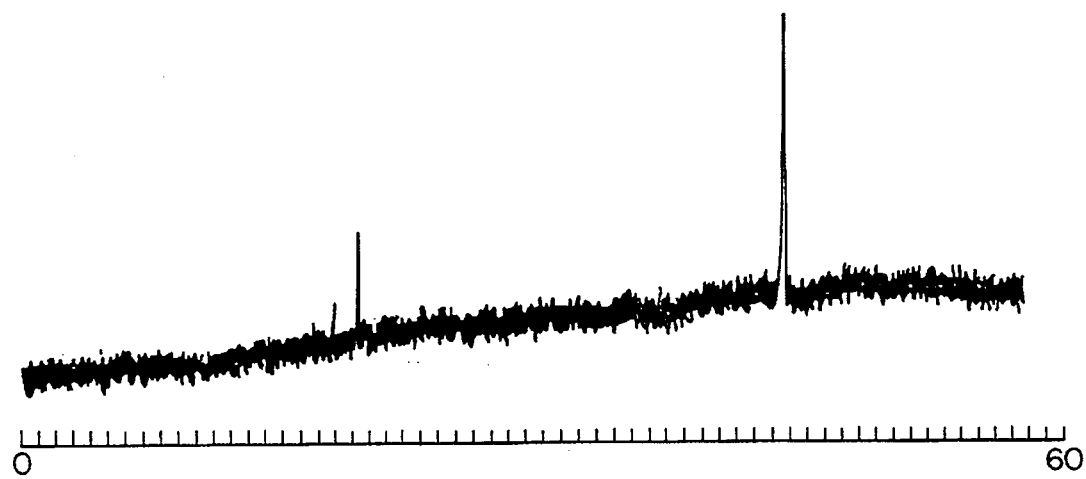
FIG. 4 is an electropherogram showing the DNA banding profile of an HPRT-Munich mutant exon 3 fragment using 7% monomer linear polyacrylamide in 7M urea at 60° C.

FIG. 4 shows the electropherogram from an experiment in which the HPRT-Munich DNA (approximately $10^8$ copies) was run on a capillary column at an elevated temperature of 60° C. The early major peak appears at about 19 minutes somewhat earlier than seen in the wild type experiment. A late peak, appearing at between 43 and 44 minutes post-injection is believed to represent the partially denatured form of the HPRT-Munich duplex fragment.

It is known that the HPRT-Munich fragment melts at a lower temperature than the wild type HPRT. This reasonably explains the fact that the wild type peak appears earlier on the electropherogram than the HPRT-Munich peak. Assuming that the wild type and mutant fragments which comprise the late peaks in FIGS. 3 and 4, respectively, migrate in conformational equilibrium between the denatured and duplex forms in the low melting domain, it is reasonable to postulate that the equilibrium form of the wild type will be shifted toward the fully duplexed form relative to the HPRT-Munich. This is due to the fact that the wild type has a greater tendency toward the fully duplexed state by virtue of its higher melting temperature relative to the mutant. The fully duplexed form migrates more quickly in the capillary matrix, and, therefore, the late peak in FIG. 3 appears about 4–5 minutes earlier than the late peak in FIG. 4.

It also appears that single stranded wild type and mutant species were separated to some lesser extent as shown by early peaks at about 18 and 20 minutes, respectively. Such a separation would not be unexpected given the fact that such similar variations are used in the single stranded conformational polymorphism technology.

Figure 5:
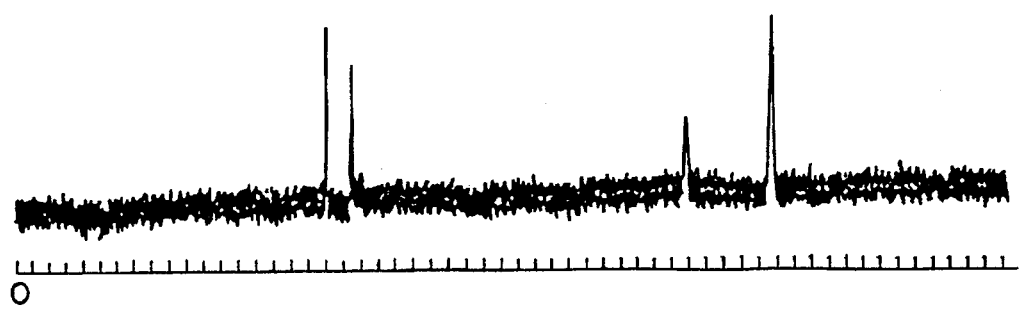
FIG. 5 is an electropherogram showing the DNA banding profile of a mixture of a wild type HPRT exon 3 fragment using 7% monomer linear polyacrylamide in 7M urea at 60° C. Here it may be seen that the different melting temperature of the low iso-melting domain has led to a clear separation of the mutant and non-mutant homoduplexes.

FIG. 5 shows an electropherogram of a mixture of the wild type HPRT fragment and the mutant HPRT-Munich fragment. The mixture is about 1:1 with the total number of fragments being about $10^8$. Four peaks appear in FIG. 5. The two early peaks passed the detector at time points almost identical to the peaks comprising fully duplexed and fully single-stranded as described in connection with FIGS. 3, 4 and 5. The first passes the detector at between 38 and 39 minutes and represents the wild-type HPRT fragment in its partially melted duplex form. The second of the late peaks appears at between 43 and 44 minutes and represents the partially melted duplex form of the HPRT-Munich fragment. Thus, the constant denaturing conditions used in the present method result in separation of the double-stranded DNA species contained in the sample (i.e., mutant/wild type heteroduplexes, mutant/mutant homoduplexes and wild type/wild type homoduplexes) via differential migration rates caused by equilibrium melting differences.

In another embodiment of the present invention, the viscosity of the polymer matrix is reduced by lowering the concentration of acrylamide used to approximately 6% and, if they are used, modifying the type and concentration of denaturing chemicals used (e.g., 3.3M urea and 20% formamide). This moderately viscous polymer matrix forms the basis of the "replaceable polymer matrix". It is now possible to replace this matrix by the simple expedient of blowing out the depleted matrix and introducing fresh matrix after each sample run. This procedure permits a highly reproducible condition for each sample run.

Figure 6:
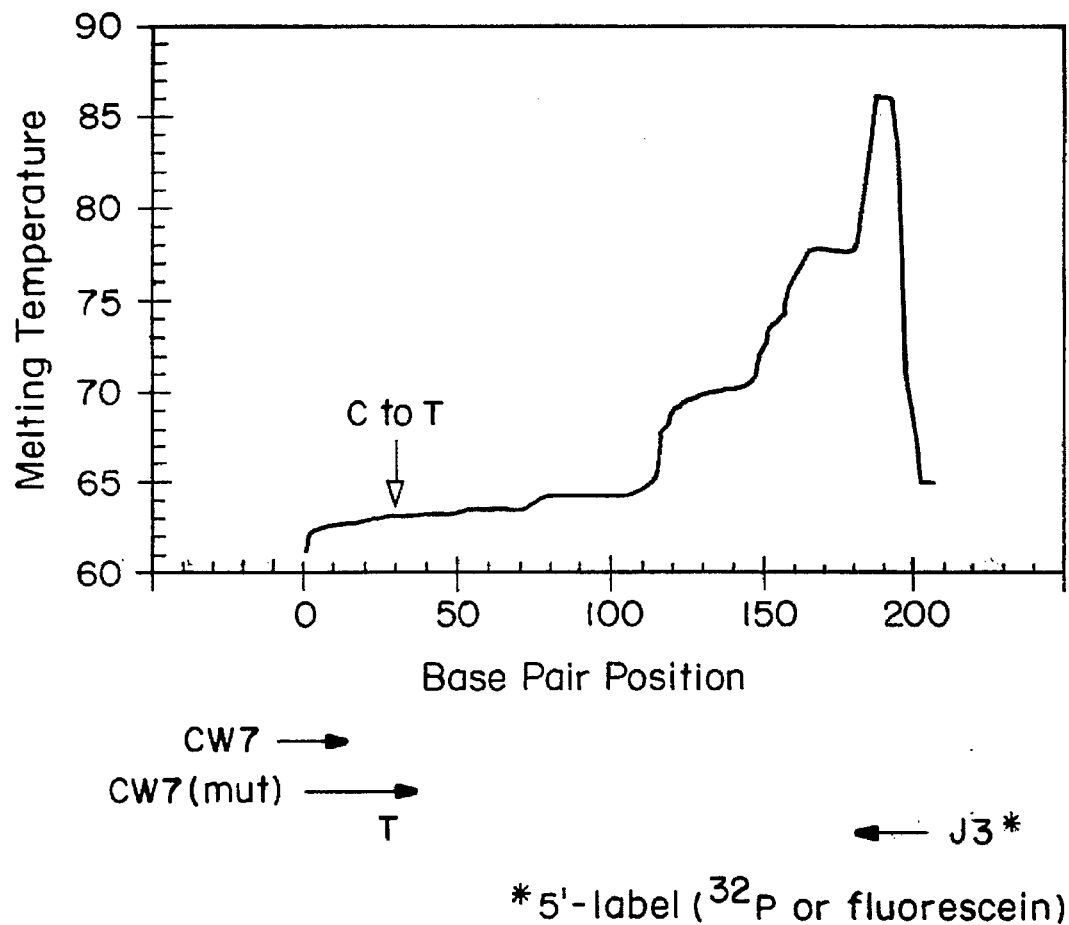
FIG. 6 shows a melting map of a non-mutant human mitochondrial DNA fragment designated CW7, J3, and the positions of PCR primers. The vertical arrow indicates the position of a single base pair difference CW7 and CJ3 respectively, in the sequences used to test the present invention. Base pair one on the map corresponds to bp 10,011 of the human mitochondrial genome.

Example 2 compares the results of conventional denaturing gradient gel electrophoresis (DGGE) and constant denaturant capillary electrophoresis (CDCE) using a replaceable polymer matrix. A 206 bp DNA sequence was identified in the human mitochondrial genome which had a contiguous low temperature melting domain (112 bp) and a high temperature melting domain (94) bp which upon partial melting would permit the separation of low temperature melting domain heteroduplexes from wild type homoduplexes. Two sequences differing by a single base pair were used to illustrate the method. The first, designated GC, had a GC base pair 30 bp from the terminus of the low melting domain, while the second designated AT had an AT base pair on this position. The melting map of the wild type (GC) fragment is shown in FIG. 6. For DGGE, both of these sequences were PCR amplified by the same set of primers, CW7 (low melting domain) and J3 (high melting domain), and purified by PAGE, as described in Example 2.

Heating and reannealing an equimolar mixture of GC and AT sequences created four species, the two homoduplexes plus mismatched heteroduplexes, resulting from the cross hybridization of GC and AT. These two heteroduplexes are called GT and AC, respectively. In some cases, single stranded DNA obtained by heating without reannealing was also included in the sample.

Figure 7:
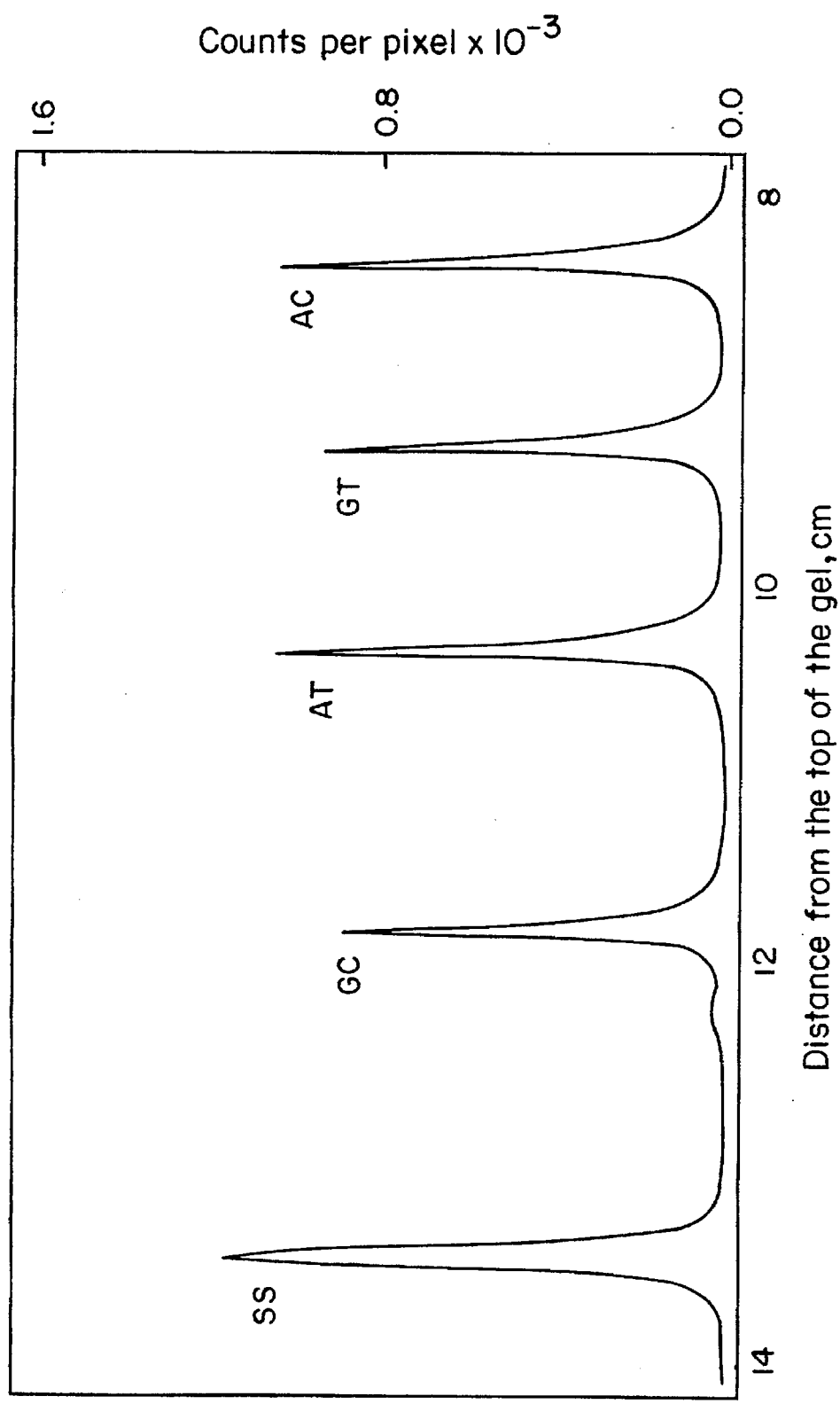
FIG. 7 shows conventional slab-gel denaturing gradient gel electrophoresis (DGGE) separation using the sequence of FIG. 6. An equimolar mixture of two homoduplexes (GC and AT) and two heteroduplexes (GT and AC). ss=single-stranded fragment.

FIG. 7 shows the separation of the four species by conventional slab-gel DGGE using radioactive detection with $^{32}$P. Samples were run under standard DGGE conditions, optimized for the separation of these particular sequences, as described in Example 2. As shown in FIG. 7, the non-reannealed single-stranded fragment (ss) migrates the furthest, followed by the reannealed fragments in the order of thermal stability of the low temperature melting domain of GC>AT>GT>AC.

The identity of GC and AT homoduplexes and single stranded DNA was determined by running pure species in separate lanes. To identify the two heteroduplex peaks, fluorescein labelled AT (the strand of the homoduplex containing A was labelled) was reannealed with unlabelled GC. This procedure creates fluorescein labelled AT and AC, but GC and GT would be unlabelled. The DGGE separation of the fluorescein labelled mixture next to $^{32}$P labelled fragments in adjacent lanes showed that the AC heteroduplex migrated the same distance as the least stable DGGE band.

Figure 8:
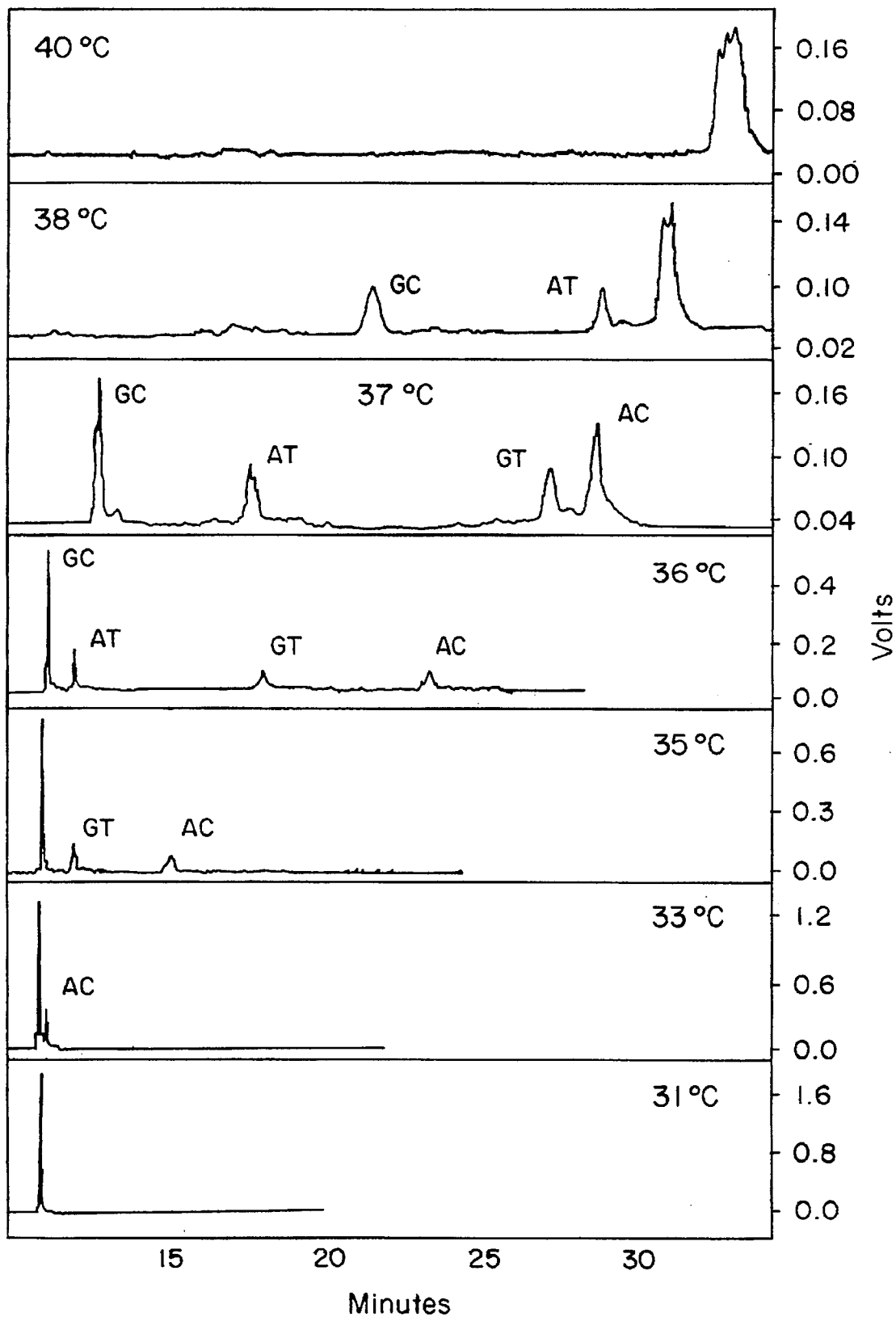
FIG. 8 shows a series of electropherograms showing constant denaturant capillary electrophoresis (CDCE) separation as a function of column temperature.

FIG. 8 demonstrates important aspects of constant denaturant capillary electrophoresis through an examination of the role of capillary column temperature on the peak pattern. The same sample as in FIG. 7, except for the absence of single stranded DNA, was prepared using fluorescein labelled DNA fragments and run on a capillary column at several temperatures, listed on each electropherogram. (See Example 2.) An equal amount of sample was injected per run. The capillary polymer matrix was 6% T linear polyacrylamide with a running buffer containing 3.3M urea and 20% (v/v) formamide in TBE. The electric field was 250 V/cm.

The effect of temperature on the particular DNA sequence of interest is shown in FIG. 8. As shown in the figure, at 31° C., a single peak is observed. This peak contains all four duplexes in the unmelted form. At 33° C., an extra peak is obtained that migrates more slowly than dsDNA. This peak is the most unstable of all four duplexes, the heteroduplex AC. (The identity of the peaks in FIG. 8 was determined in a similar manner to that described for FIG. 7).

Increasing the temperature to 35° C. results in another slowly moving peak, the GT heteroduplex. At 36° C., four peaks are observed, the two homoduplexes GC and AT, as well as the two heteroduplexes GT and AC. As the temperature rises to 37° C., 38° C. and 40° C., the separation varies until all four species have identical slow velocities. This was interpreted to mean that all four species were fully converted to the partially melted form in the denaturing zone and, thus, had identical velocities in the electrophoretic field.

Assuming that the partial melting/reannealing process occurs rapidly, the migration time of each band will be dependent on the equilibrium constant K of the partial melting process.

$$K = \frac{X_{pm}}{X_{um}} \quad (1)$$

where X is the mole fraction and subscripts pm and um are the partially melted and the unmelted fragments. The electrophoretic velocity (v) of a species in the denaturing zone can be written as $$v = x_{UM} v_{UM} + x_{PM} v_{PM}$$

where $v_{um}$ and $v_{pm}$ are velocities of unmelted and partially melted fragments, respectively. It is clear from equations (1) and (2) that as K increases with temperature in the denaturing zone, the velocity of a DNA species will decrease from $v_{um}$ to $v_{pm}$ (in FIG. 8, $v_{um} \sim 4 v_{pm}$). It is worth noting that by measuring u as a function of temperature, along with the values of $v_{pm}$ and $v_{um}$, one can obtain the thermodynamic parameters of DNA melting equilibrium inside the capillary.

Based on the results described above, a simple procedure can be utilized to detect mutations in a specific DNA sequence of approximately 100–200 base pairs. The approximate melting temperature of the low temperature iso-melting domain can be first calculated using Lerman's algorithm, with appropriate correction for the concentration of denaturant (Lerman, L. S. and Silverstein, K., Meth. Enzymol. 155:482–501 (1987)). This estimated temperature can then be refined by performing test runs of the wild type sequence at different temperatures. The optimal temperature for the separation of the homoduplexes would be that at which the wild type sequence is 50% partially melted (as for GC at 38° C. in FIG. 8), and the optimal temperature for the heteroduplexes would be the one at which the wild type is just slightly melted (as for GC at 36° C. in FIG. 8). Each cycle of separation can be completed in only 5–10 minutes so that optimization could be completed in roughly ½ hour. Note also that this optimization procedure does not require any prior information about expected mutants, other than sequence.

Critical to the success of the method described herein was the ability to create a fresh matrix after each run. In a series of experiments to attempt to find the cause of this effect it was found that duplex instability varied among different DNA preparations and also appeared to worsen when the same capillary column was used in attempts at serially analyzing DNA samples. The experiments led to the explanation in terms of varied salt concentration in the DNA samples combined with the advance of a region of high resistance through the column trailing each DNA sample. In a first sample this effect was small but in subsequent attempts the low resistance region with concomitant local heating was apparently responsible for the DNA duplex instability. However, samples were injected a second time into the column after a run of approximately 30, reproducibility of migration times for the partially melted form was poor (20% or worse). It should be noted that, in Example 1, either the top of the capillary was cut off prior to each run, or the entire capillary was replaced, to achieve the described results. These observations led to the method described herein of loading DNA into the polymer matrix at a fixed low ionic strength combined with physically replacing the polymer matrix after each run, a process as simple as a syringe injection. Using replaceable matrices, good migration time reproducibility was observed from run-to-run, with reproducibilities approximately ±2% relative standard deviation. Since the melting temperature will be quite sensitive to the medium (e.g. ionic strength), linear polyacrylamide matrix/buffer replacement after each run provides a highly reproducible medium for maintaining constant the fraction of a species that is partially melted. Moreover, as an additional advantage, in the replaceable polymer matrix format, buffer and matrix conditions can be rapidly changed when desired.

As a significant example of changes that can occur in a column, if samples were injected a second time into the column under the conditions of FIG. 8, only a peak of the single-stranded fragment was obtained, as confirmed by injection of a predenatured sample. Upon matrix replacement, the appropriate four peak pattern was again observed.

The reason for the appearance of a peak of the single stranded fragment with the second injection into a "used", or depleted, matrix may be the formation of a zone of low conductivity found at the cathodic end of the capillary. The zone is due to transference number differences for buffer ions in the bulk solution and the sieving matrix. Since the voltage drop across this small zone will be high, Joule heating will occur, and this heat will likely be sufficient, under this condition, to melt the DNA fragments fully to single stranded species. Probably, the melting temperature was also reduced in this low conductivity "hot zone" due to low ionic strength, and this aided the denaturing of dsDNA.

A striking feature illustrated by the results shown in FIG. 8 is the significant increase in peak width of the partially melted DNA fragments relative to the unmelted form (even after correction for mobility differences). Since resolution (defined as the difference in migration times for two species divided by their average peak width) of the partially melted forms is important for the separation of mixtures of mutated sequences, the role of several operational parameters on resolution in terms of the separation of the two heteroduplexes GT and AC was investigated.

Figures 9A, 9B, 9C:
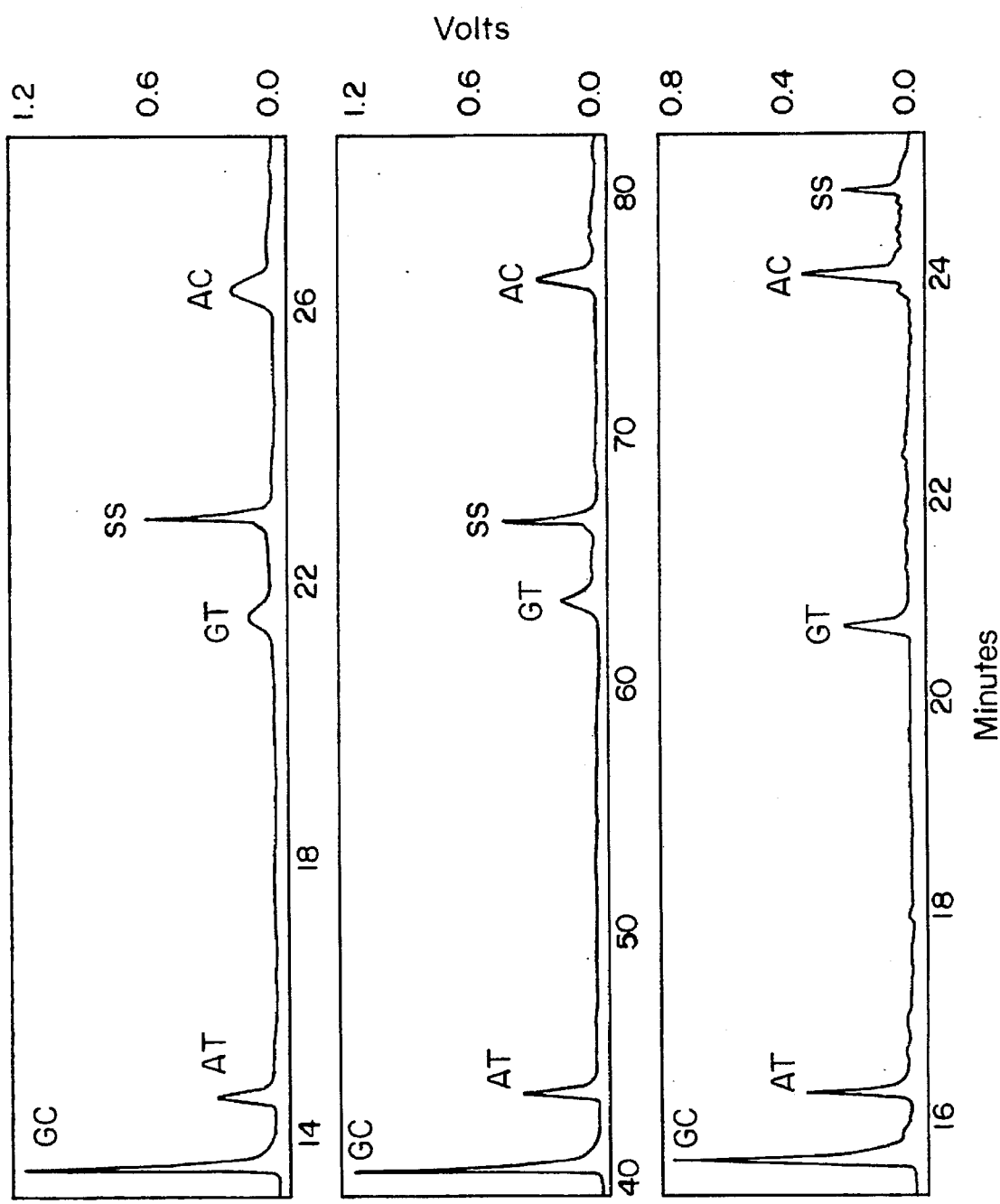
FIG. 9A is an electropherogram of mutant/nonmutant heteroduplexes obtained with a matrix of 6% T at 36° C., 250 V/cm with a running buffer containing 3.3M urea and 20% (v/v) formamide in TBE.
FIG. 9B is an electropherogram of mutant/nonmutant heteroduplexes obtained with a matrix of 6% T at 36° C., 83 V/cm with a running buffer containing 3.3M urea and 20% (v/v) formamide in TBE.
FIG. 9C is an electropherogram of mutant/nonmutant heteroduplexes obtained with a matrix of 6% T at 63° C., 125 V/cm and running buffer TBE in the absence of denaturant.

FIG. 9A, 9B, and 9C shows a series of electropherograms illustrating the role of electric field and temperature on resolution. The sample, with the addition of 5% single stranded DNA (ss), was run as follows: (A) at 36° C., conditions as in FIG. 8; (B) as in (A), but at 83 V/cm and (C) with a matrix of 6% T at 63° C. and 125 V/cm, running buffer TBE, in the absence of denaturant. To permit visual comparison of the electropherograms, the time axes of the three runs are adjusted such that the bands appear to coincide.

It is first noted that extending the time spent by the bands in the denaturant zone (FIG. 9B) results in an improvement in resolution of 1.6 fold over that in FIG. 9A. Comparable resolution to that in FIG. 9A was found when the time spent by the bands in the heated portion of the capillary was extended to the same extent by increasing the length of the denaturant zone 3-fold, that is, including more of the capillary within the heated zone, at a field of 250 V/cm. This increase in resolution with time in the denaturant zone is due to narrower peak widths (normalized to the migration time) for the heteroduplexes, as seen in FIG. 9B. Band widths for the partially melted forms are thus controlled by kinetic processes rather than by diffusional processes. Such slow kinetics could arise from interactions of the partially melted form with the linear polyacrylamide or by the melting/reannealing process itself.

Based on this finding, a higher temperature was tested. FIG. 9C shows the result of operating at 63° C. with no denaturant in the polymer matrix. Relative to FIG. 9A, resolution is improved by 2.6 fold, due again primarily to the sharper bands, at no increase in separation time. The elevated temperature accelerated the rate limiting kinetic process, leading to narrower bands. Note also that the position of ssDNA has shifted in FIG. 9C due to the different operating conditions.

Figures 10A, 10B, 10C:
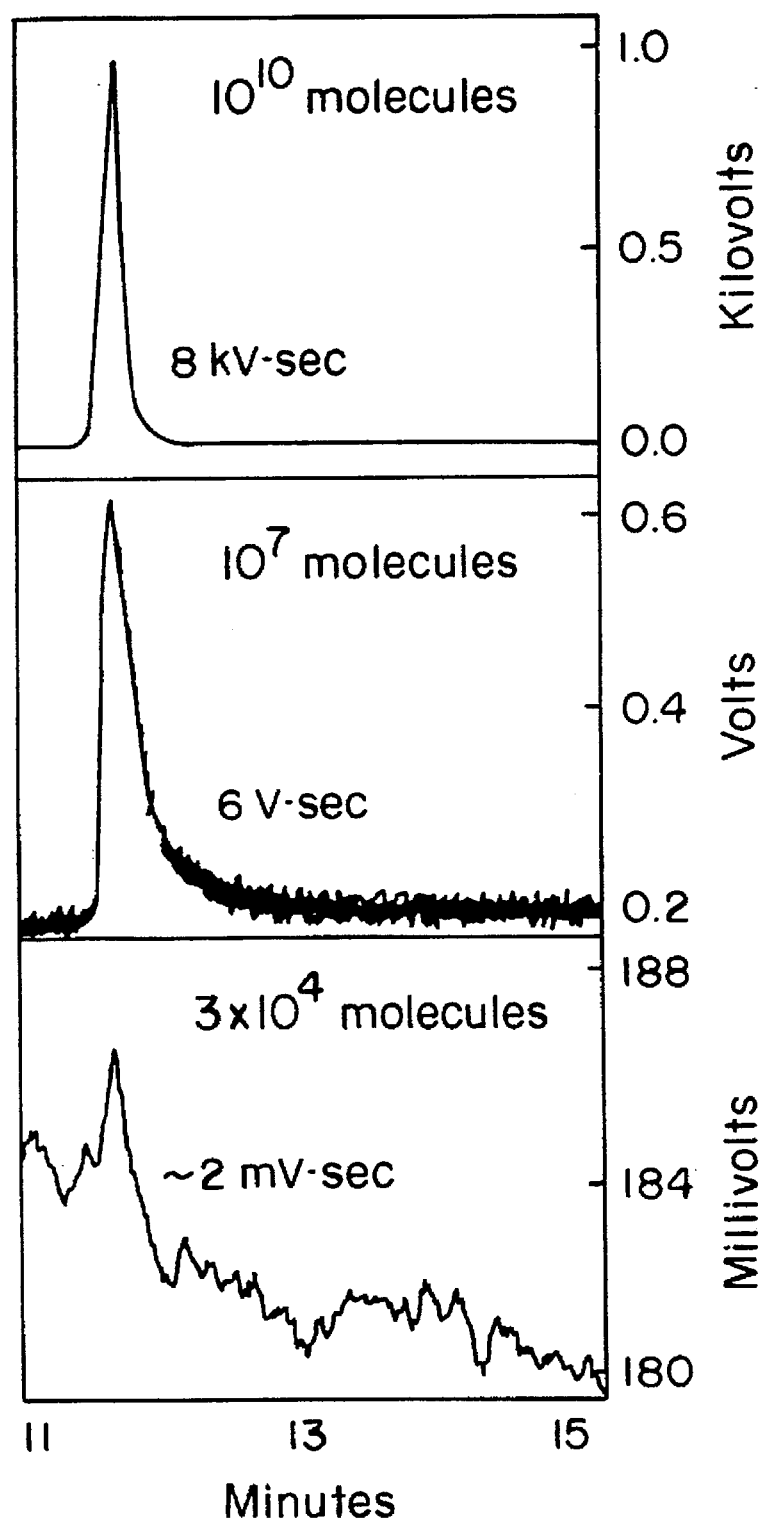
FIG. 10A shows an electropherogram of $10^{10}$ molecules of GC homoduplex injected into a capillary from 0.2 µl samples and run at ambient temperature.
FIG. 10B shows an electropherogram of $10^7$ molecules of GC homoduplex injected into a capillary from 0.2 µl samples and run at ambient temperature.
FIG. 10C shows an electropherogram of $3\times10^4$ molecules of GC homoduplex injected into a capillary from 0.2 µl samples and run at ambient temperature.

As demonstrated in the Examples laser-induced fluorescence (LIF) provides a sensitive means to detect small numbers of DNA molecules labelled with fluorescent dyes. Nevertheless, in some cases (including mutational spectrometry) the ability to load large amounts of DNA is also critical. For determining the dynamic range (e.g., the range of ability to detect a number of molecules) in the present system, the indicated amounts of GC homoduplex were injected into the capillary from 0.2 µl samples and run at ambient temperature (22° C.). The results are shown in FIG. 10. For $10^{10}$ copies, the laser beam was attenuated 10 times and amplification was 1/10 of the regular. For $3\times10^4$ copies, the laser power was increased 5 times, and the noise was filtered by averaging across 10 second intervals surrounding each point of the curve. (Note that peak areas are included with the electropherograms). As many as $10^{11}$ copies were loaded and measured. However, loading more than $10^{10}$ molecules led to peak distortion. A peak of $3\times10^4$ copies of dsDNA is still visible above the system background. Calibration plots of number of molecules vs. peak area were found to be close to linear throughout the range of $3\times10^4$–$10^{11}$ molecules.

Figure 11:
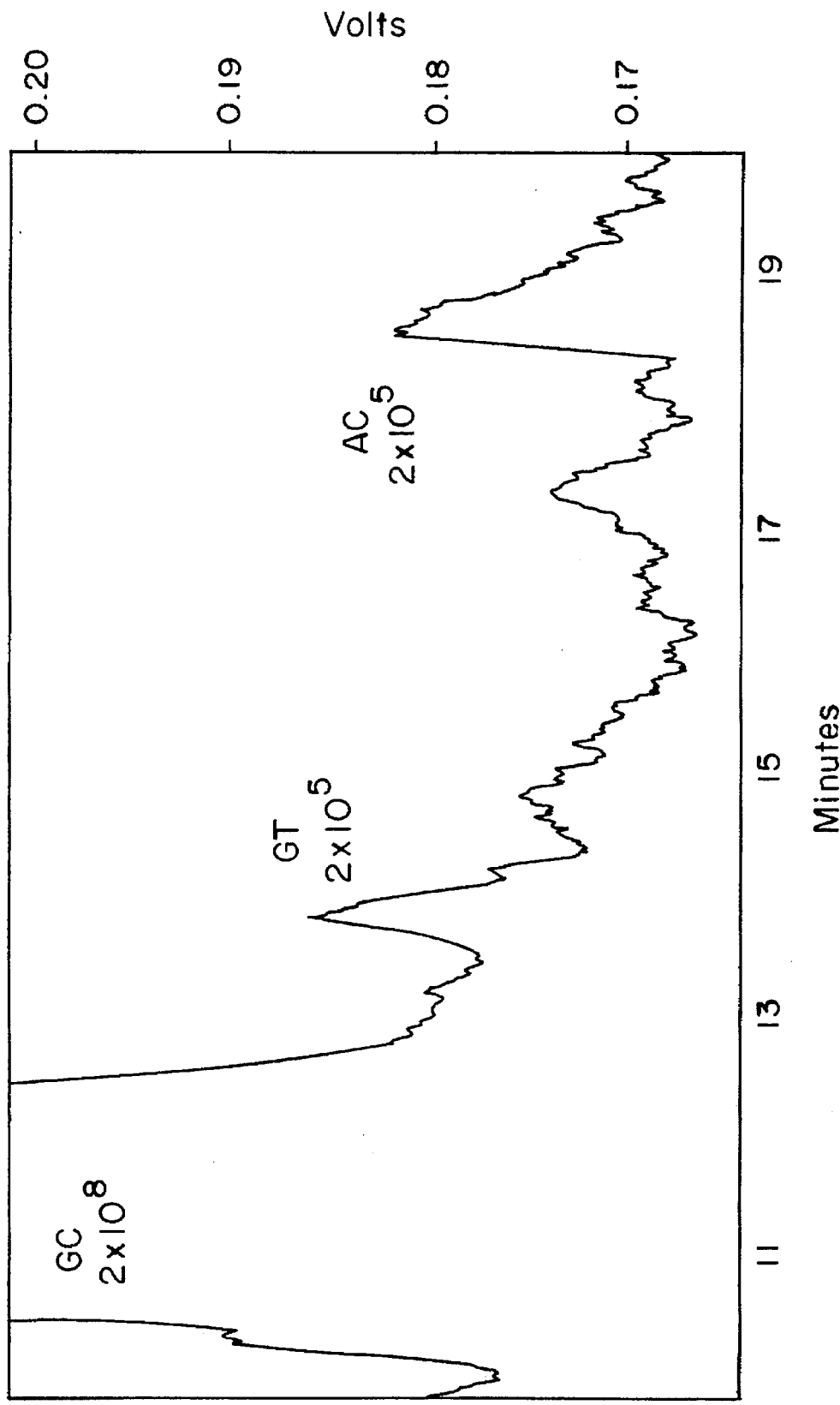
FIG. 11 shows an electropherogram depicting detection of small mutant fractions ($3\times10^{-4}$) in the presence of large excess of wild type DNA.

While even lower detection levels are in principle possible, a more critical measure of detection is the fraction of a mutant that can be observed in the presence of a large excess of wild type homoduplexes. FIG. 11 demonstrates that as small as 0.03% admixture of mutant heteroduplexes to the wild type homoduplex can be determined using the method of the present invention. AC and GT mutant heteroduplexes, $3\times10^5$ copies each, were admixed to with a large excess ($10^9$) of copies of wild type GC homoduplex and run on a capillary at 35° C. (replaceable matrix with denaturant). In contrast to that shown in FIG. 10, the background noise seen in FIG. 11, which interferes with identification of mutants present in small amounts, apparently consists of chemically reacted wild type DNA molecules.

As described in Example 3, the signal to noise ratio can be reduced significantly by subjecting a DNA sample to two cycles of constant denaturing capillary electrophoresis. GT and AC heteroduplexes, $5\times10^4$ copies each, were admixed with $10^9$ copies of wild type homoduplex and subjected to CDCE. The fractions containing the separated heteroduplexes were collected, amplified by high fidelity PRC, and subjected to a second cycle of CDCE. Each cycle consists of subjecting a sample to CDCE using fresh polymer matrix, collecting the fractions containing the heteroduplexes, and amplifying the collected fractions by suitable amplification means.

Figure 12A:
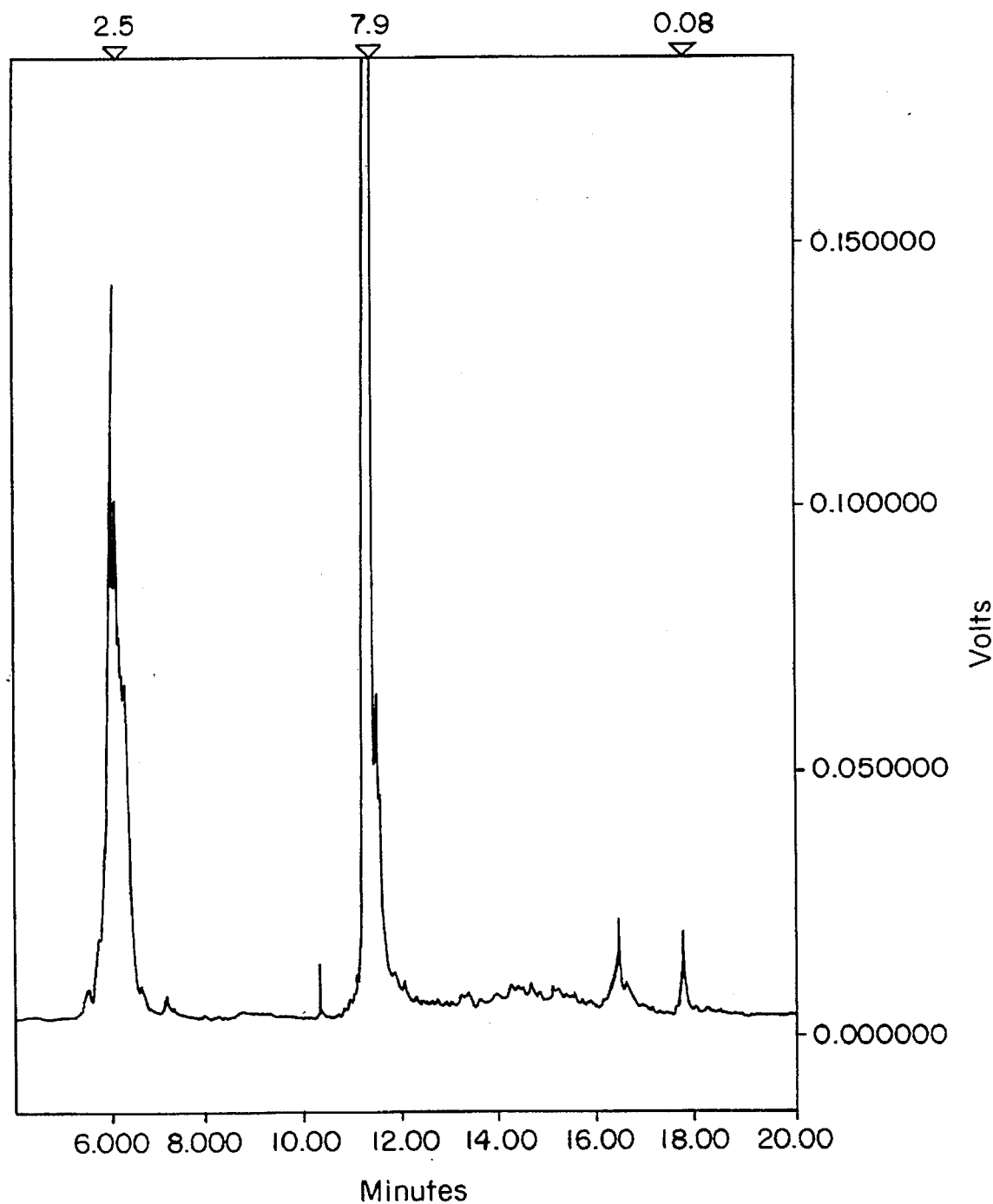
FIG. 12A shows a capillary electropherogram depicting the detection of heteroduplexes after a single cycle of CDCE/PRC amplification.
Figure 12B:
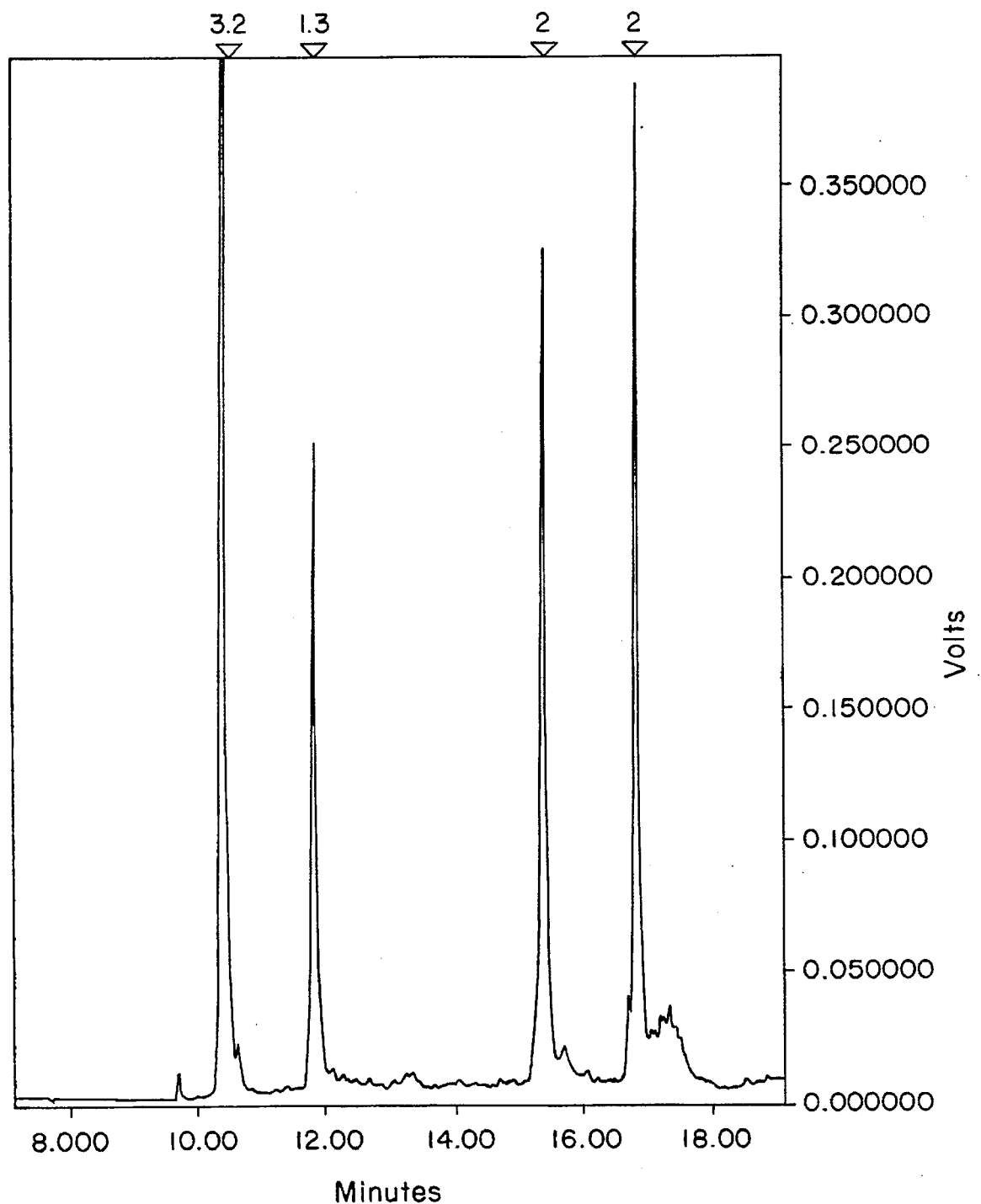
FIG. 12B shows a capillary electropherogram depicting the detection of heteroduplexes after suitable amplification and a second cycle of CDCE/PRC amplification.

In FIG. 12A, it should be noted that the heteroduplex-containing peaks, appearing at approximately 16.5 and 18.0 minutes, are some ten times larger than the noise peaks. In FIG. 12B, after a second cycle of CDCE, the heteroduplex containing peaks are some 100 times larger than the noise peaks. A key observation is that the level of background noise did not co-amplify with amplification of the heteroduplex-containing fractions. This indicates that as few as $5\times10^{-6}$ mutants could have been detected in the original standard sample.

Uses of the Invention

The method described herein is useful in any biotechnological application where detection of mutant nucleic acid sequences is important. Any DNA which contains a mutation in a low temperature iso-melting domain is suitable for separation by the method described herein. This method of separation is particularly suitable for detection of mutant DNA which represents a small fraction of total DNA present in a sample. In particular, the method described herein is useful for analysis of DNA or RNA sequences to be used in gene therapy, analysis of plasmid DNA, analysis of recombinant DNA or recombinant plant DNA, detecting somatic mutants at specific DNA loci, such as in mutational spectrometry, and for screening of tissues for premalignant mutants.

Oncology

In the detection of cancer cells the oncologist seeks early diagnosis of a new tumor, or in the case of a discovered tumor the extent of cancer cell immigration (metastasis) or reemergence after chemotherapy or radiotherapy. Furthermore, it is now known that certain specific mutations in tumor suppressor genes predispose persons to the early occurrence of certain tumors. The present invention will permit detection and measurement of such rare sequences in a practical and efficient manner.

Screening Cancer Prone Populations

In the case of rare inherited oncomutations, PCR amplification of the DNA contained in a blood or tissue sample, and sequencing the result could reveal whether or not a mutation is present in the individual and DNA sequence sampled (if the mutation is present at a frequency that can be detected in this manner). However, only one in ten thousand individuals may carry any of several such mutations in the sequence examined. With the present invention, laboratories may combine microliter aliquots of blood from each of a thousand samples and assay for the presence of one or more mutation carriers in any of the nucleotides of the DNA sequence assayed. Identification of the afflicted individual may then be performed by a few trials of subpopulation samples, eliminating the normal sequence carries.

Cancer Cell Detection

The present invention may be applied to the DNA of any human tissue or bodily fluid including feces (detection of colon cancer) urine (detection of bladder cancer) sputum (detection of bronchial cancer) blood (detection of leukemia, lymphoma, etc.) or breast aspirate (mammary carcinoma). The analytic method allows screening of significant sizes of DNA fragments, thus, increasing its probability of detecting cancer cells in addition to its intrinsic sensitivity of detecting any mutant of the DNA sequence studied. The advantage of the present method over other methods that are specific for a particular base pair substitution, is that an oncogene is aimed at "more probable" oncomutants rather than "all possible" oncomutants of a tumor suppressor gene. With the present method, all possible oncomutants can be detected in a desired sequence.

In addition to early detection in cases of undiagnosed cancer, the method of this invention may be applied in clinical pathology to judge the extent of metastasis or recurrence of the disease. Such knowledge obtained in a timely fashion is believed to increase the efficacy of therapeutic measures. An example is the examination of axial lymph nodes which drain the mammary gland. When breast cancer begins to spread, a few cells will be caught in these lymph nodes and are recognizable by a certified pathologist using standard techniques, such as analysis of differentially stained tissue samples. More aggressive therapeutic measures are indicated if such lymph node involvement has occurred. The present invention could detect a mutant DNA sequence common to the cancer cells at frequencies well below that which would be visible in stained tissue samples. For a tumor suppressor gene such as p53, which is frequently found to be mutated among cells of a cancer, the present method has been used to detect one mutant in a thousand. The method presented herein, coupled with suitable methods of DNA amplification, may even allow measurement of mutants in such lymph node samples on a time scale which might permit decisions on the extent of surgical resection while the patient is still under anesthesia for biopsy.

Cancer chemotherapy is essentially an attempt to kill every cell of a tumor. If one cell, or a few cells, survive treatment they can grow to reestablish a tumor. Early recognition of growth of these cells is believed to contribute to the success of subsequent therapy. The present method, coupled with knowledge of particular mutations of the patient, would allow routine and effective screening of patients for such relapses. This method would permit use of the same apparatus and materials for the monitoring of many patients carrying oncomutations in any known oncogene or tumor suppressor gene.

Finally, the speed and simplicity of the method facilitates studies on the thermodynamics and kinetics of melting of nucleic acids and DNA binding interactions with other DNA or RNA sequences, as well as DNA-protein interactions governed by cooperative equilibria.

Thus, as a result of the work presented herein, a new method for mutational analysis has been provided. The method is rapid, with excellent resolution of partially melted species. The method provides a superior means to enrich the fraction of mutant DNA contained in a mixed sample of wild type and mutant DNA. Moreover, further enrichment can be obtained by subsequent recycling of the enriched sample. Such recycling is critical for the study of mutant fractions below $10^{-3}$, especially in the range of $10^{-8}$ to $10^{-3}$.

The method described herein is highly sensitive, with a wide, linear dynamic range using laser induced fluorescence detection. In particular, the method described herein is readily computerized and automated. Moreover, high throughput of sample can be achieved by parallel processing of multiple channel arrays.

The present invention will now be illustrated by the following Examples, which are not to be seen limiting in any way.

Example 1: Electrophoresis of HPRT
Preparation of DNA Samples

Wild type HPRT exon 3, as well as the HPRT-Munich exon 3 were amplified from isolated genomic DNA by a modification of the PCR methodology as shown schematically in FIG. 1B. Wild-type genomic DNA was isolated from exponentially gravity mole TK6 human lymphoblasts (see e.g. Porteous, *Somat. Cell. Mol. Genet.* 11:445–454 (1985). The following primers were employed in the amplification procedure:

P1: 5'-CATATATTAAATATACTCAC-3' (SEQ ID NO:1);
P2: 5'-TCCTGATTTTATTTCTGTAG-3' (SEQ ID NO:2); and
P3: 5'-GACTGAACGTCTTGCTCGAG-3' (SEQ ID NO:3).

In a first round of amplification, approximately $10^6$ copies of the wild-type HPRT exon 3 and approximately $10^6$ copies of the HPRT-Munich exon 3 were amplified separately by priming amplification with unlabeled primers P1 and P2 to generate an amplification product of 224 base pairs. The DNA was amplified approximately 1 million-fold to about $10^{12}$ copies of each. Amplification was carried out using the Sequenase™ polymerase (U.S. Biochemicals) according to the manufacturer's instructions. The amplified DNA was then purified by polyacrylamide gel electrophoresis (PAGE).

Approximately $10^6$ copies of the purified 224 base pair amplification product were subjected to a second round of amplification. In the second round, synthesis was primed with primers P1 and P3 which resulted in the production of a 204 base pair DNA fragment. Primer P3 was end-labeled with fluorescein by conventional methods. Polymerization was carried out with the Vent™ polymerase (New England Biolabs) according to the manufacturer's instructions. This DNA was also amplified approximately one million-fold.

The 204 base pair fragment was subjected to two rounds of purification to remove any polymerase induced mutations. The first purification round was by PAGE. The 204 base pair band was cut from the acrylamide gel and eluted by conventional methods. The second round of purification was by denaturing gradient gel electrophoresis (DGGE) (see e.g. Cariello et al., *Am. J. Mum. Genet.* 42:726–734 (1988)). Prior to loading the DNA on the denaturing gradient matrix, the 204 base pair fragments were denatured. Both the wild type HPRT and the HPRT-Munich derived 204 base pair fragment were boiled in separate tubes to denature the DNA. The denatured DNA was then incubated at 65° C. for approximately 3 hours to permit reannealing. The reannealed product was ethanol precipitated, resuspended, and separated on a denaturing gradient gel. Wild type HPRT fragment and HPRT-Munich fragment were cut from the denaturing gradient gel, eluted, ethanol precipitated and resuspended in water. The concentration of these samples was diluted to a concentration of about $10^8$ copies per microliter.

Capillary Electrophoresis Apparatus

The capillary electrophoresis system used in this work was configured as described by Cohen et al. (*Proc. Natl. Acad. Sci. USA* 85:9660 (1988)) except that a 60 kV high voltage d.c. power supply was used to generate the potential across the matrix filled capillary.

The laser detection system employed is similar to that described by Kuhr and Yeung (*Anal. Biochem.* 60:2642 (1988)). An argon ion laser mounted on a 4×6 foot optical table was operated in the light-regulated mode at 8–10 mW. The laser light was passed through a narrow band pass filter directed by reflection using a beam steerer and focused into the capillary with a 24-turn focal length lens. Fluorescence from the sample was collected with a 40× microscope objective and passed through an interference filter and a colored glass filter. A photomultiplier tube operated at 700 V and a photomultiplier readout were used to detect fluorescence. The resulting voltage output was displayed on a strip chart recorder and was simultaneously transmitted to an analog-to-digital (A/D) interface for transfer to a PC.

A temperature heating device was made of two ceramic blocks in which the capillary was sandwiched. A 75 Watt heater and temperature controller were installed in the block to heat and to control the block temperature. Over 80% of the capillary was sandwiched between the two ceramic blocks and heated to the desired temperature. Model numbers and manufacturers of the above-listed components are supplied in Cohen et al., *J. Chromatog.* 516:49–60 (1990).

Capillary Column

Capillary electrophoresis was performed in fused-silica tubing (Polymicro Technologies, Phoenix, Ariz.) 75 μm inner diameter, 375 μm OD, effective length (1)=320–350 mm, total length (L)=500 mm. Capillaries were prepared as described by Heiger et al. (*J. Chromatog.* 516:33–48 (1990) ). Briefly, methacryloxypropyl-trimethoxy silane was first covalently bound to the fused-silica capillary walls. A solution of acrylamide (7% T, 0% C) in 0.1M Tris-borate (pH 8.2), 2.5 mM EDTA and 7M urea was prepared, degassed and introduced in the treated capillary following the addition of ammonium persulfate (APS) and N, N, N',N'- tetramethylethylenediamine (TEMED). Samples were injected into the column by dipping the cathodic end of the capillary into the sample solution and applying a voltage of 300 V/cm for 10–20 seconds. Separation was achieved at a typical applied field of 300 V/cm.

Example 2: Constant Denaturant Capillary Electrophoresis with Replaceable Matrix The instrumentation was similar to that described in Example 1. Briefly, the power supply was 30 kV dc (Model CZE 1000R-2032, Spellman, Plainview, N.Y.). A low power argon ion laser (Omnichrome, Chino, Calif.) was run at 5 mW. The vertical laser beam was filtered through a 488 nm (10 nm bandwidth) filter (Corion, Holliston, Mass.), and focused into the horizontal separation capillary. The focusing lens, capillary and objective were mounted onto 3-D micropositioners, and the system was placed on an optical bench. Emitted light was collected by a microscopic objective (Oriel, Stamford, Conn.) at right angles to both the capillary and the beam and directed through two 520 nm (10 nm bandwidth) filters (Corion) into a photomultiplier (Oriel). The signal from the photomultiplier was amplified ($10^8$ V/A) by a current preamplifier (Oriel) to 10 V full scale and recorded by a 16 bit data acquisition system (MP100, Biopac Systems, Goleta, Calif.).

Capillary Electrophoretic Conditions

Electrophoresis was performed at various electric fields in 75 μm ID, 350 μm OD capillaries (Polymicro Technologies, Inc., Phoenix, Ariz.), coated as described in Example 1, and filled with 5%–6% linear polyacrylamide, 3.3M urea, 20% (v/v) formamide in TBE (89 mM Tris, 89 mM boric acid and 1 mM EDTA, pH 8.3). In one example, FIG. 9C, the chemical denaturants, urea and formamide, were omitted.

Acrylamide was polymerized in 10 ml glass syringes under conditions favoring formation of long polymer chains. After polymerization was completed, the syringe could be stored at −15° C. for several weeks. Linear polyacrylamide from a 10 ml syringe was dispensed into 100 μl high pressure gas-tight syringes (Hamilton, Reno, Nev.) as needed. The syringes were used to replace the polyacrylamide matrix before each run. Typically, a capillary was used for several weeks and withstood hundreds of injections.

In cases where the exact amount of DNA injected into a capillary was important, e.g., for calibration of the detector, samples of 0.2 μl in water or dilute buffer (not higher than 0.1×TBE) were electro-injected into a capillary (1 μA for 2 min) from a 350 μm I.D. Teflon robe mounted onto the injection end of the capillary. Once the detector was calibrated, the samples were injected directly from a larger sample volume (typically 5 μl) by applying currents of the order of 1 μA for several seconds. When necessary, as much as 85% of DNA material from 2 μl samples could be injected in one injection (1 μA for 2 min).

Denaturing Gradient Matrix Electrophoresis (DGGE) Preparation of DNA

Total DNA was isolated from frozen human male TK-6 lymphoblasts. For DGGE the fragments of interest were amplified with Pfu DNA polymerase (Stratagene, La Jolla, Calif.) according to the manufacturer's protocol, purified by standard 8% PAGE and quantified by ethidium bromide staining. The primers were as follows:

CW7 5'-ACCGTTAACTTCCAATTAAC (SEQ ID NO:4); CW7mut 5'-ACCGTTAACTTCCAATTAACTAGTTTTGATAACAT-TCAAA (SEQ ID NO:5); and 5'-fluorescein labelled, as well as non-labelled J3 5'-ATGGAGAAAGGGACGCGGGC (SEQ ID NO:6) were obtained from Synthetic Genetics (San Diego, Calif.). In the case of radioactive detection on DGGE, J3 was γ labelled with $^{32}$P prior to PCR amplification. To introduce a GC to AT substitution, the primer CW7mut, which formed a T:C mismatch with the template at position 30, was substituted for CW7 in a PCR reaction. The introduction of the point mutation was confirmed by sequencing of the PCR product. For boiling and reannealing, DNA in water was heated to 100° C. for 10 sec, then adjusted to 200 mM NaCl, 10 mM Tris HCl pH 8, 2 mM EDTA and incubated at 60° C. for 2 hours. Equimolar mixture of two homoduplexes (GC and AT) and two heteroduplexes (GT and AC) was run under standard DGGE conditions on a slab matrix, optimized for the separation of these particular sequences: 16 hours run at 60° C.; matrix: 12% acrylamide, 0.4% bis-acrylamide, 1×TAE; 20 cm long linear denaturant gradient: top:6% (v/v) formamide, 1.05M urea, bottom 14% (v/v) formamide, 2.8M urea. DNA was end labeled with $^{32}$P; the matrix was dried and scanned with a Phosphoimager (Molecular Dynamics).

The results of DGGE separation were compared to results of CDCE separation as described above.

Example 3: Constant Denaturant Capillary Electrophoresis with Replaceable Matrix With Repeat Cycle The DNA sample was prepared as described in Example 2. Mutant/wild type heteroduplexes of each of two possible pairs (GT and AC) were mixed with wild type/wild type homoduplexes, resulting in a sample mixture containing $10^9$ wild type/wild type (WT/WT) homoduplex plus 5×$10^4$ of each heteroduplex.

This mixture was separated by constant denaturant capillary electrophoresis under the conditions described in Example 2. The fractions containing the mutant/WT heteroduplexes (fractions appearing from approximately 14 to 20 minutes) were collected, amplified by high fidelity polymerase chain reaction and the mixture subjected to constant denaturant capillary electrophoresis using fresh polymer matrix. As seen in FIG. 12A, four distinct peaks appear in the electropherogram. The peak appearing at approximately 6.0 minutes represents an internal standard (PCR primer). The peak appearing at approximately 11.0 minutes represents WT/WT homoduplex. The peaks appearing at approximately 16.5 and 18.0 minutes represent the GT and AC mutant/WT heteroduplexes, respectively.

The fractions containing the heteroduplexes were again collected, pooled amplified and subjected to CDCE separation. The results are shown in FIG. 12B. The peak appearing at approximately 10.5 minutes represents WT/WT homoduplex, the peak appearing at approximately 12.0 minutes represents mutant/mutant homoduplex, and the peaks appearing at approximately 15 and 17 minutes represent the GT and AC heteroduplexes.

Equivalents

Those skilled in the art will know, or be able to ascertain using no more than routine experimentation, many equivalents to the specific embodiments of the invention described herein. These and all other equivalents are intended to be encompassed by the following claims.

The invention claimed is:

1. A method of resolving mutant DNA from non-mutant DNA in a DNA sample which, as obtained or modified, contains double stranded mutant DNA and double stranded non-mutant DNA, each with two iso-melting domains, a first iso-melting domain referred to as a low temperature iso-melting domain, which melts at a first temperature and a second iso-melting domain, referred to as a high temperature iso-melting domain, which melts at a second, higher temperature, wherein the mutant DNA contains a mutation of interest in the low temperature iso-melting domain, comprising the steps of:

a) isolating the DNA sample from a biological source;
  b) fragmenting DNA in the DNA sample isolated in a) to obtain fragmented double-stranded DNA of interest;
  c) melting and reannealing the fragmented double-stranded DNA of interest obtained in step b) under conditions appropriate to form duplexed DNA, thereby producing a mixture of DNA heteroduplexes and DNA homoduplexes;
  d) introducing the mixture produced in step c) into a replaceable polymer matrix contained within a capillary column, thereby producing a replaceable polymer matrix containing the mixture of DNA heteroduplexes and DNA homoduplexes;
  e) subjecting the replaceable polymer matrix containing the mixture of DNA heteroduplexes and DNA homoduplexes to a high electrical field and partially denaturing conditions, wherein the partially denaturing conditions are constant denaturing conditions, whereby the DNA heteroduplexes partially melt and the DNA homoduplexes do not melt and the DNA heteroduplexes migrate at a slower velocity in the replaceable polymer matrix then the DNA homoduplexes, resulting in the separation of DNA heteroduplexes from DNA homoduplexes.

2. A method of claim 1, wherein step b) further comprises partially isolating the fragmented double-stranded DNA of interest by size separation.

3. A method of claim 1 further comprising a detecting step wherein the detecting step is selected from the group consisting of: a) detecting the relative positions of DNA heteroduplexes and DNA homoduplexes within the polymer matrix at a specified time, b) detecting the relative movement of DNA heteroduplexes and DNA homoduplexes as they pass a fixed position detector; and c) detecting the relative movement of DNA heteroduplexes and DNA homoduplexes as they exit from the polymer matrix.

4. A method of claim 3 further comprising collecting fractions of the DNA heteroduplexes and DNA homoduplexes as they exit the polymer matrix and determining the nucleotide sequences of the duplexes contained within the collected fractions.

5. A method of claim 4 further comprising amplifying the duplexes in the collected fractions prior to sequencing.

6. A method of claim 1, wherein the fragmented double-stranded DNA of step b) is obtained by digesting the isolated DNA of interest with appropriately selected restriction endoucleases.

7. A method of claim 1, wherein in step e), the partially denaturing conditions comprise the presence of chemical denaturants in the polymer matrix and a polymer matrix temperature of approximately 24° C. to approximately 100° C., and the high electrical field is approximately 50 to approximately 1200 volts/cm.

8. A method of claim 1, wherein in step e), the polymer matrix does not contain chemical denaturants, the partially denaturing condition comprises a polymer matrix temperature from approximately 24° C. to approximately 100° C., and the high electric field is from approximately 50 to approximately 1200 volts/cm.

9. A method of resolving mutant DNA from non-mutant DNA in a DNA sample, which, as obtained or modified, contains double stranded mutant DNA and double stranded non-mutant DNA, each with one iso-melting domain but the iso-melting domain is not contiguous with an iso-melting domain of higher thermal stability, comprising the steps of:

a) isolating the DNA sample from a biological source;
  b) fragmenting DNA in the DNA sample in step a) to obtain fragmented double-stranded DNA of interest;
  c) partially isolating the fragmented DNA of interest by size separation to obtain partially isolated DNA fragments;
  d) attaching to the fragmented DNA of interest partially isolated in c) a DNA sequence which is an iso-melting domain of higher thermal stability than the iso-melting domain contained in the DNA as obtained, thereby producing DNA fragments of interest which comprise DNA sequences which contain an iso-melting domain contiguous with an iso-melting domain of higher thermal stability;
  e) melting and reannealing the DNA fragments obtained in step d) under conditions appropriate to form duplexed DNA, thereby producing a mixture of DNA heteroduplexes and DNA homoduplexes;
  f) introducing the mixture obtained in step e) into a replaceable polymer matrix contained within a capillary column, thereby producing a replaceable polymer matrix containing the mixture of DNA heteroduplexes and DNA homoduplexes;
  g) subjecting the replaceable polymer matrix in the capillary column containing the mixture of DNA heteroduplexes and DNA homoduplexes to a high electrical field and partially denaturing conditions, wherein the partially denaturing conditions are constant denaturing conditions, whereby the DNA heteroduplexes partially melt and the DNA homoduplexes do not melt and the DNA heteroduplexes migrate at a slower velocity in the replaceable polymer matrix than the DNA homoduplexes, resulting in the separation of DNA heteroduplexes from DNA homoduplexes.

10. A method of claim 9 further comprising a detecting step wherein the detecting step is selected from the group consisting of: a) detecting the relative positions of DNA heteroduplexes and DNA homoduplexes within the polymer matrix at a specified time, b) detecting the relative movement of DNA heteroduplexes and DNA homoduplexes as they pass a fixed position detector; and c) detecting the relative movement of DNA heteroduplexes and DNA homoduplexes as they exit from the polymer matrix.

11. A method of claim 10 further comprising collecting fractions of the DNA heteroduplexes and DNA homoduplexes as they exit the polymer matrix and determining the nucleotide sequences of the duplexes contained within the collected fractions.

12. A method of claim 11 further comprising amplifying the duplexes in the collected fractions prior to sequencing.

13. A method of claim 9, wherein the fragmented double-stranded DNA of step b) is obtained by digesting the isolated DNA of interest with appropriately selected restriction endonucleases.

14. A method of claim 9, wherein the fragmented double-stranded DNA of step b) is labeled with a detectable reporter group.

15. A method of claim 9, wherein in step g), the partially denaturing conditions comprise the presence of chemical denaturants in the polymer matrix and a polymer matrix temperature of approximately 24° C. to approximately 100° C., and the high electrical field is approximately 50 to approximately 1200 volts/cm.

16. A method of claim 9, wherein in step g), the polymer matrix does not contain chemical denaturants, the partially denaturing condition comprises a polymer matrix temperature from approximately 24° C. to approximately 100° C., and the electric field is from approximately 50 to approximately 1200 volts/cm.

17. A method of resolving mutant DNA from non-mutant DNA in a DNA sample which, as obtained or modified, contains double stranded mutant DNA and double stranded non-mutant DNA, each with one iso-melting domain but the iso-melting domain is not contiguous with an iso-melting domain of higher thermal stability, comprising the steps of:
  a) isolating the DNA sample from a biological source;
  b) fragmenting DNA in the DNA sample to obtain fragmented double-stranded DNA of interest;
  c) partially isolating the fragmented DNA by size separation to obtain partially isolated DNA fragments;
  d) melting and reannealing the DNA fragments obtained in step c) with synthetic DNA comprising the non-mutant DNA sequence containing an iso-melting domain as obtained with a DNA sequence of higher thermal stability attached thereto, under conditions appropriate to form duplexed DNA comprising two DNA strands, one strand being shorter than the other strand;
  e) extending the shorter strand of the duplexed DNA obtained in step d) with DNA polymerase to produce duplexes comprising two strands of the same length, thereby producing a mixture of DNA heteroduplexes and DNA homoduplexes comprising DNA containing an iso-melting domain contiguous with an iso-melting domain of higher thermal stability;
  f) introducing the mixture obtained in step e) into a replaceable polymer matrix contained within a capillary column, thereby producing a replaceable polymer matrix containing the mixture of DNA heteroduplexes and DNA homoduplexes;
  g) subjecting the replaceable polymer matrix containing the mixture of DNA heteroduplexes and DNA homoduplexes to a high electrical field and partially denaturing conditions, wherein the partially denaturing conditions are constant denaturing conditions, whereby the DNA heteroduplexes partially melt and the DNA homoduplexes do not melt and the DNA heteroduplexes migrate at a slower velocity in the replaceable polymer matrix than the DNA homoduplexes, resulting in the separation of DNA heteroduplexes from DNA homoduplexes.

18. A method of claim 17 further comprising a detecting step wherein the detecting step is selected from the group consisting of: a) detecting the relative positions of DNA heteroduplexes and DNA homoduplexes within the polymer matrix at a specified time, b) detecting the relative movement of DNA heteroduplexes and DNA homoduplexes as they pass a fixed position detector; and c) detecting the relative movement of DNA heteroduplexes and DNA homoduplexes as they exit from the polymer matrix.

19. A method of claim 18 further comprising collecting fractions of the DNA heteroduplexes and DNA homoduplexes as they exit the polymer matrix and determining the nucleotide sequences of the duplexes contained within the collected fractions.

20. A method of claim 17, wherein the fragmented double-stranded DNA of step b) is obtained by digesting the isolated DNA of interest with appropriately selected restriction endonucleases.

21. A method of claim 17, wherein the fragmented double-stranded DNA of step b) is labeled with a detectable reporter group.

22. A method of claim 17, wherein in step g), the partially denaturing conditions the presence of chemical denaturants in the polymer matrix and a polymer matrix temperature of approximately 24° C. to approximately 100° C., and the high electrical field is approximately 50 to approximately 1200 volts/cm.

23. A method of claim 17, wherein in step g), the polymer matrix does not contain chemical denaturants, the partially denaturing condition comprises a polymer matrix temperature from approximately 24° C. to approximately 100° C., and the electric field is from approximately 50 to approximately 1200 volts/cm.

24. A method of resolving mutant DNA from non-mutant DNA in a DNA sample which, as obtained or modified, contains double stranded mutant DNA and double stranded non-mutant DNA which both lack a suitable iso-melting domain, comprising the steps of:
  a) isolating the DNA sample of interest from a biological source;
  b) fragmenting DNA in the DNA sample to obtain fragmented double-stranded DNA of interest;
  c) partially isolating the fragmented DNA by size separation to obtain partially isolated DNA fragments;
  d) attaching to one end of the fragmented DNA of interest partially isolated in step c) a DNA sequence which is an iso-melting domain of higher thermal stability than the fragmented DNA, and to the other end, a DNA sequence which is an iso-melting domain which melts at, or near, the average melting temperature of the fragmented DNA sequence thereby producing DNA fragments which comprise a suitable iso-melting domain containing the DNA sequence of interest contiguous with an iso-melting domain of higher thermal stability;
  e) melting and reannealing the DNA fragments of interest obtained in step d) under conditions appropriate to form duplexed DNA, thereby producing a mixture of DNA heteroduplexes and DNA homoduplexes;
  f) introducing the mixture obtained in step e) into a replaceable polymer matrix contained within a capillary column, thereby producing a replaceable polymer matrix containing the mixture of DNA heteroduplexes and DNA homoduplexes;
  g) subjecting the replaceable polymer matrix containing the mixture of DNA heteroduplexes and DNA homoduplexes to a high electrical field and partially denaturing conditions, wherein the partially denaturing conditions are constant denaturing conditions, whereby the DNA heteroduplexes partially melt and the DNA homoduplexes do not melt and the DNA heteroduplexes migrate at a slower velocity in the polymer matrix than the DNA homoduplexes, resulting in the separation of DNA heteroduplexes from DNA homoduplexes.

25. A method of claim 24 further comprising a detecting step wherein the detecting step is selected from the group consisting of: a) detecting the relative positions of DNA heteroduplexes and DNA homoduplexes within the polymer matrix at a specified time, b) detecting the relative movement of DNA heteroduplexes and DNA homoduplexes as they pass a fixed position detector; and c) detecting the relative movement of DNA heteroduplexes and DNA homoduplexes as they exit from the polymer matrix.

26. A method of claim 25 further comprising collecting fractions of the DNA heteroduplexes and DNA homoduplexes as they exit the polymer matrix and determining the nucleotide sequences of the duplexes contained within the collected fractions.

27. A method of claim 24, wherein the fragmented double-stranded DNA of step b) is obtained by digesting the isolated DNA of interest with appropriately selected restriction endonucleases.

28. A method of claim 24, wherein the fragmented double-stranded DNA of step b) is labeled with a detectable reporter group.

29. A method of claim 24, in step g), wherein the partially denaturing conditions comprise the presence of chemical denaturants in the polymer matrix and a polymer matrix temperature of approximately 24° C. to approximately 100° C., and the high electrical field is approximately 50 to approximately 1200 volts/cm.

30. A method of claim 24, wherein in step g), the polymer matrix does not contain chemical denaturants, the partially denaturing condition comprises a polymer matrix temperature from approximately 24° C. to approximately 100° C., and the electric field is from approximately 50 to approximately 1200 volts/cm.

31. A method of resolving mutant DNA from non-mutant DNA in a DNA sample which, as obtained or modified, contains double stranded mutant DNA and double stranded non-mutant DNA, each with two iso-melting domains, a first iso-melting domain referred to as low temperature iso-melting domain, which melts at a first temperature and a second iso-melting domain, referred to as a high temperature iso-melting domain, which melts at a second, higher temperature and wherein the mutant DNA contains a mutation of interest is in the low temperature iso-melting domain, comprising the steps of:

a) isolating the DNA sample from a biological source;

b) fragmenting the DNA in DNA sample to obtain fragmented double-stranded DNA of interest;

c) melting and reannealing the double-stranded DNA fragments obtained in step b) under conditions appropriate to form duplexed DNA, thereby producing a mixture of DNA heteroduplexes and DNA homoduplexes;

d) introducing the mixture obtained in step c) into a replaceable polymer matrix contained in a capillary column, thereby producing a replaceable polymer matrix containing the mixture of DNA heteroduplexes and DNA homoduplexes;

e) subjecting the replaceable polymer matrix containing the mixture of DNA heteroduplexes and DNA homoduplexes to a high electrical field and partially denaturing conditions, wherein the partially denaturing conditions are constant denaturing conditions, whereby the DNA heteroduplexes partially melt and the DNA homoduplexes do not melt and the DNA heteroduplexes migrate at a slower velocity in the replaceable polymer matrix than the DNA homoduplexes, resulting in the separation of DNA heteroduplexes from DNA homoduplexes;

f) detecting the relative movement of the DNA heteroduplexes and DNA homoduplexes as they exit from the replaceable polymer matrix and collecting fractions containing the DNA heteroduplexes and DNA homoduplexes as they exit from the replaceable polymer matrix;

g) removing the replaceable polymer matrix from the channel and introducing fresh replaceable polymer matrix into the channel; and h) reintroducing the DNA heteroduplexes collected in step f) into the fresh replaceable polymer matrix, thereby producing a fresh replaceable polymer matrix containing DNA heteroduplexes and subjecting the fresh replaceable polymer matrix to a high electrical field and, as in step e), collecting fractions containing the DNA heteroduplexes as they exit from the fresh replaceable polymer matrix.

32. A method of claim 31, wherein step f) further comprises amplifying the DNA heteroduplexes collected in fractions by a suitable amplification method prior to step h).

33. A method of claim 31, wherein step f) through step h) is repeated one, or more, times resulting in enrichment of the DNA heteroduplexes in the collected fractions.

34. A method of claim 31, wherein step h) further comprises determining the DNA sequence of the DNA heteroduplexes collected in the fractions.

35. A method of claim 31, wherein step h) further comprises amplifying the DNA heteroduplexes collected in the fractions by a suitable amplification method and determining the DNA sequence of the DNA heteroduplexes.

36. A method of screening a DNA sample for mutations which, as obtained or modified, contains non-mutant DNA and is suspected of containing mutant DNA, wherein the mutant DNA and the non-mutant DNA contain two iso-melting domains, a first iso-melting domain, referred to as a low-temperature iso-melting domain, which melts at a first temperature, and a second iso-melting domain, referred to as a high temperature iso-melting domain, which melts at a second, higher temperature and the mutant DNA contains a mutation of interest in the low temperature iso-melting domain, comprising the steps of:

a) isolating the DNA sample from a biological source;

b) fragmenting DNA in the DNA sample to obtain fragmented double-stranded DNA of interest;

c) labeling the fragmented DNA of interest obtained in step b) with a detectable reporter group thereby producing labeled DNA of interest;

d) melting and reannealing the labeled DNA of interest under conditions appropriate to form duplexed DNA, thereby producing DNA heteroduplexes, if mutant DNA is present, and DNA homoduplexes;

e) introducing the duplexes produced in step d) into a replaceable polymer matrix contained within a capillary column;

f) subjecting the replaceable polymer matrix containing the DNA duplexes to a high electrical field and partially denaturing conditions, wherein the partially denaturing conditions are constant denaturing conditions, whereby if DNA heteroduplexes are present, the DNA heteroduplexes partially melt and the DNA homoduplexes do not melt and the DNA heteroduplexes migrate at a slower velocity in the replaceable polymer matrix than the DNA homoduplexes, resulting in the separation of DNA heteroduplexes from DNA homoduplexes; and g) detecting the relative movement of the DNA heteroduplexes, if present, and DNA homoduplexes as they exit from the replaceable polymer matrix and collecting fractions containing the DNA heteroduplexes, if present, and DNA homoduplexes as they exit from the replaceable polymer matrix, wherein the presence of DNA heteroduplexes is indicative of the presence of mutations in the DNA sample.

37. A method of claim 36 further comprising:

h) removing the polymer matrix from the capillary column and introducing fresh matrix into the capillary column;

i) reintroducing the DNA heteroduplexes collected in step g) into the fresh polymer matrix, thereby producing a fresh polymer matrix containing DNA heteroduplexes and subjecting the polymer matrix to a high electrical field as in step f) and collecting fractions containing the DNA heteroduplexes as they exit from the polymer matrix.

38. A method of claim 36, wherein step g) further comprises amplifying the DNA heteroduplexes collected in the fractions by a suitable amplification method.

39. A method of claim 36, wherein step g) through step i) is repeated one, or more, times resulting in enrichment of the DNA heteroduplexes in the collected fractions.

40. A method of claim 36, wherein step i) further comprises determining the DNA sequence of the DNA heteroduplexes.

41. A method of claim 36, wherein step i) further comprises amplifying the DNA heteroduplexes collected in the fractions by a suitable amplification method and determining the DNA sequence of the DNA heteroduplexes.

42. A method of claim 36, wherein the denaturing conditions of step d) comprise the presence of chemical denaturants in the polymer matrix and a polymer matrix temperature of approximately 24° C. to approximately 100° C., and the high electrical field is approximately 50 to approximately 1200 volts/cm.

43. A method of claim 36, wherein the polymer matrix does not contain chemical denaturants, the partially denaturing condition comprises a polymer matrix temperature from approximately 24° C. to approximately 100° C., and the electric field is from approximately 50 to approximately 1200 volts/cm.

44. A method for resolving two or more species of double-stranded DNA fragments which differ by at least one base pair, the double-stranded DNA fragments comprising two iso-melting domains, a first iso-melting domain, referred to as a low-temperature iso-melting domain, which melts at a first temperature, and a second iso-melting domain, referred to as a high temperature iso-melting domain, which melts at a second, higher temperature and the mutant DNA contains a mutation of interest in the low temperature iso-melting domain, comprising the steps of:

a) providing a liquid sample containing two or more species of double-stranded DNA fragments which differ by at least one base pair labeled with a fluorescent reporter group;

b) melting and reannealing the labeled double-stranded DNA fragments under conditions appropriate to form duplexed DNA, thereby producing a mixture of labeled DNA heteroduplexes and labeled DNA homoduplexes;

c) introducing the labeled mixture of duplexes produced in step b) into a replaceable polymer matrix contained within a capillary column thereby producing a replaceable polymer matrix containing the mixture of DNA heteroduplexes and DNA homoduplexes;

d) subjecting the replaceable polymer matrix containing the mixture of DNA heteroduplexes and DNA homoduplexes to constant denaturant capillary electrophoresis whereby the DNA heteroduplexes partially melt and the DNA homoduplexes do not melt and the DNA heteroduplexes migrate at a slower velocity in the replaceable polymer matrix than the DNA homoduplexes resulting in the separation of DNA heteroduplexes from DNA homoduplexes;

e) detecting the relative movement of the labeled DNA heteroduplexes and labeled DNA homoduplexes as they exit the replaceable polymer matrix by exposing an end portion of the capillary column to light energy of a wavelength appropriate for the stimulation of fluorescence of the fluorescent reporter group and detecting the fluorescence with a detector thereby detecting the relative movement of the separated labeled DNA duplexes as they exit the replaceable polymer matrix; and f) collecting fractions containing the labeled DNA heteroduplexes as they exit the replaceable polymer matrix.

45. A method of claim 44 further comprising:

g) removing the polymer matrix from the capillary column and introducing fresh matrix into the capillary column;

h) reintroducing the DNA heteroduplexes collected in step f) into the fresh polymer matrix and subjecting the polymer matrix to a constant denaturing capillary electrophoresis as in step d) and collecting fractions containing the DNA heteroduplexes as they exit from the polymer matrix.

46. A method of claim 44, wherein step f) further comprises amplifying the DNA heteroduplexes collected in the fractions by a suitable amplification method.

47. A method of claim 45, wherein step f) through step h) is repeated one, or more, times resulting in enrichment of the DNA heteroduplexes in the collected fractions.

48. A method of claim 44, wherein step h) further comprises determining the DNA sequence of the DNA heteroduplexes.

49. A method of claim 44, wherein step h) further comprises amplifying the DNA heteroduplexes collected in the fractions by a suitable amplification method and determining the DNA sequence of the DNA heteroduplexes.

50. A method of claim 44, wherein the denaturing conditions of step e) comprise the presence of chemical denaturants in the polymer matrix and a polymer matrix temperature of approximately 24° C. to approximately 100° C., and the high electrical field is approximately 50 to approximately 1200 volts/cm.

51. A method of claim 44, wherein the polymer matrix does not contain chemical denaturants, the partially denaturing condition comprises a polymer matrix temperature from approximately 24° C. to approximately 100° C., and the electric field is from approximately 50 to approximately 1200 volts/cm.

* * * * *

UNITED STATES PATENT AND TRADEMARK OFFICE
CERTIFICATE OF CORRECTION

PATENT NO. : 5,633,129
DATED : May 27, 1997
INVENTOR(S) : Barry L. Karger et al.

It is certified that error appears in the above-indentified patent and that said Letters Patent is hereby corrected as shown below:

On title page, item

[75] Inventors:

after "Roger W. Giese, Quincy," insert --Alexei Belinkii, Newton--.

Claim 31, line 39: delete "is".

Signed and Sealed this

Twenty-first Day of April, 1998

Attest:

BRUCE LEHMAN

*Attesting Officer*  *Commissioner of Patents and Trademarks*

Disclaimer

5,633,129—Barry L. Karger, Newton; William G. Thilly, Winchester; Frantisek Foret, Malden; Konstaintin Khrapko, Brookline, all of Mass; Phouthone Koehavong, Pittsburgh, Pa; Aharon S. cohen, Newton; and Roger W. Giese, Quincy, both of Mass. ELECTROPHORETIC DETECTION AND SEPARATION OF MUTANT DNA USING REPLACEABLE POLYMER MATRICES. Patent dated May 27, 1997. Disclaimer filed Mar. 13, 2006, by the assignee, Massachusetts Institute of Technology, Cambridge; Northeastern University, both of Mass.

Hereby enter this disclaimer to 15 month of said patent.

*(Official Gazette, May 9, 2006)*